(12) United States Patent
Tabuchi et al.

(10) Patent No.: US 11,028,149 B2
(45) Date of Patent: Jun. 8, 2021

(54) RECOMBINANT POLYPEPTIDE PRODUCTION METHOD

(75) Inventors: Hisahiro Tabuchi, Tokyo (JP); Tomoya Sugiyama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/008,791

(22) PCT Filed: Mar. 30, 2012

(86) PCT No.: PCT/JP2012/058577
§ 371 (c)(1),
(2), (4) Date: Sep. 30, 2013

(87) PCT Pub. No.: WO2012/137683
PCT Pub. Date: Oct. 11, 2012

(65) Prior Publication Data
US 2014/0030758 A1    Jan. 30, 2014

(30) Foreign Application Priority Data

Apr. 1, 2011 (JP) .............................. JP2011-082002

(51) Int. Cl.
| | | |
|---|---|---|
| *C07K 16/00* | (2006.01) | |
| *C12N 15/113* | (2010.01) | |
| *A61K 38/00* | (2006.01) | |
| *C07K 16/30* | (2006.01) | |
| *C07K 16/28* | (2006.01) | |

(52) U.S. Cl.
CPC ............ *C07K 16/00* (2013.01); *C12N 15/113* (2013.01); *A61K 38/00* (2013.01); *C07K 16/2866* (2013.01); *C07K 16/303* (2013.01); *C07K 2317/14* (2013.01); *C12N 2310/14* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 2007/0050146 A1* | 3/2007 | Bentwich et al. | ............... 702/19 |
| 2009/0297436 A1* | 12/2009 | Garcia-Martinez | .......................... C07K 16/248 424/1.11 |
| 2010/0167346 A1 | 7/2010 | Tabuchi et al. | |
| 2010/0233759 A1 | 9/2010 | Tabuchi et al. | |
| 2011/0003334 A1 | 1/2011 | Tabuchi et al. | |

FOREIGN PATENT DOCUMENTS

| | | |
|---|---|---|
| CN | 101454345 A | 6/2009 |
| EP | 1270044 A2 | 1/2003 |
| EP | 1 674 111 A1 | 6/2006 |
| WO | 94/10305 A1 | 5/1994 |
| WO | WO 02/31114 A2 | 4/2002 |
| WO | WO 2006/105109 A2 | 10/2006 |
| WO | WO-2007/143168 A2 | 12/2007 |
| WO | WO 2008/114673 A1 | 9/2008 |
| WO | WO 2009/020144 A1 | 2/2009 |
| WO | WO 2009/051109 A1 | 4/2009 |

OTHER PUBLICATIONS

Takasaki (Methods Mol Biol. 2013;942:17-55).*
Martinez-Sanchez et al (Biology 2013, 2, 189-205).*
Warzocha et al (Leukemia and Lymphoma, Val. 24. pp. 267-281).*
Arenzana-Seisdedos et al., "Inducible Nuclear Expression of Newly Synthesized IκBα Negatively Regulates DNA-Binding and Transcriptional Activities of NF-κB," Molecular and Cellular Biology, May 1995, 15(5):2689-2696.
Chen et al., "New Insights into the Role of Nuclear Factor-κB in Cell Growth Regulation," American Journal of Pathology, Aug. 2001, 159(2):387-397.
Cowen et al., "5-Hydroxytryptamine 1A Receptor-Mediated Increases in Receptor Expression and Activation of Nuclear Factor-κB in Transfected Chinese Hamster Ovary Cells," Mol. Pharmacol., 1997, 52:221-226.
He et al., "Synergistic activation of the CMB promoter by NF-κB P50 and PKG," Biochemical and Biophysical Research Communications, 2004, 321:13-20.
Hu et al., "From Mice to Humans: Identification of Commonly Deregulated Genes in Mammary Cancer via Comparative SAGE Studies," Cancer Research, Nov. 1, 2004, 64:7748-7755.
Lee et al., "NF-κB- and c-Jun-dependent regulation of human cytomegalovirus immediate-early gene enhancer/promoter in response to lipopolysaccharide and bacterial CpG-oligodeoxynucleotides in macrophage cell line RAW 264.7," Eur. J. Biochem., 2004, 271:1094-1105.
Lei et al., "Regulation of NF-κB inhibitor IκBα and viral replication by KSHV microRNA," Nature Cell Biology, 2010, 12(2):193-199.
NCBI Nucleotide [online], Accession No. NM_010907, Mar. 25, 2011 (retrieved on May 18, 2012), retrieved from the internet: <URL: http://www.ncbi/nlm.hin.gov.nuccore/226052095?sat=14 &satkey=6190226>, 4 pages.
Trill et al., "Production of monoclonal antibodies in COS and CHO cells," Curr. Opin. Biotechnol., 1995, 6:553-560.
Lan et al., "Suppression of IκBα increases the expression of matrix metalloproteinase-2 in human ciliary muscle cells," Molecular Vision, Sep. 22, 2009, 15:1977-1987.
Tabuchi, Hisahiro, "Novel strategy for a high-yielding mAb-producing CHO strain (overexpression of non-coding RNA enhanced proliferation and improved mAb yield)," BMC Proceedings, Dec. 4, 2013, 7(Suppl6):3, 2 pages.
Kawakami et al., "Identification and purification of a human immunoglobulin-enhancer-binding protein (NF-κB) that activates transcription from a human immunodeficiency virus type 1 promoter in vitro," Proc. Natl. Acad. Sci. USA, Jul. 1998, 85:4700-4704.

\* cited by examiner

*Primary Examiner* — Brian Gangle
*Assistant Examiner* — Andrea K McCollum
(74) *Attorney, Agent, or Firm* — Foley & Lardner LLP

(57) ABSTRACT

Provided is a method capable of producing a protein at a high level using a cultured animal cell, comprising culturing a cell that expresses APES (Antibody Production Enhancing Sequence) and into which a DNA encoding a desired polypeptide has been introduced, thereby producing the desired polypeptide. APES contains a nucleotide sequence related to nuclear factor κB inhibitor α (NfkBia) and has a function of decreasing the intracellular expression of NfkBia.

8 Claims, 16 Drawing Sheets

Specification includes a Sequence Listing.

[Figure 1]
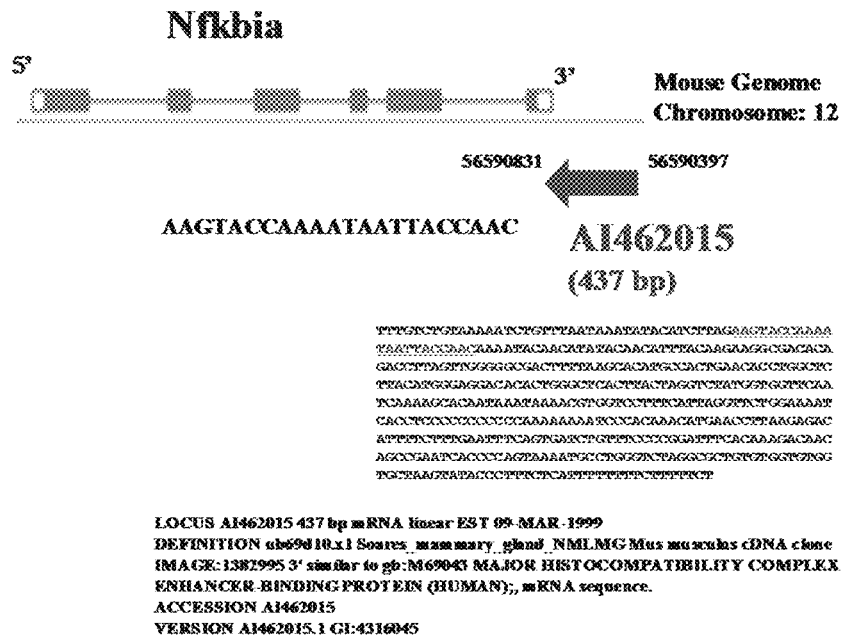
[Figure 2]
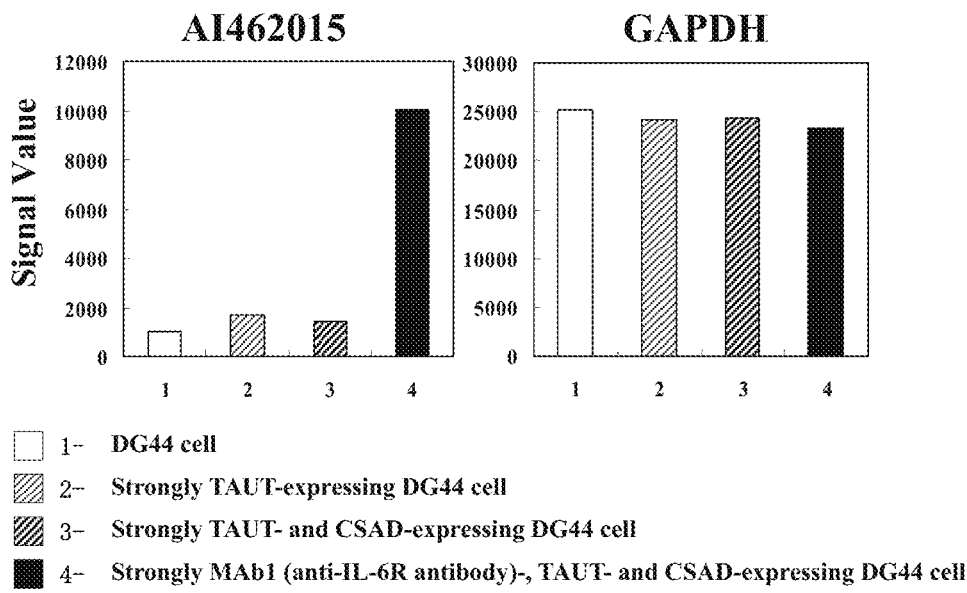
- 1 – DG44 cell
- 2 – Strongly TAUT-expressing DG44 cell
- 3 – Strongly TAUT- and CSAD-expressing DG44 cell
- 4 – Strongly MAb1 (anti-IL-6R antibody)-, TAUT- and CSAD-expressing DG44 cell

[Figure 3]
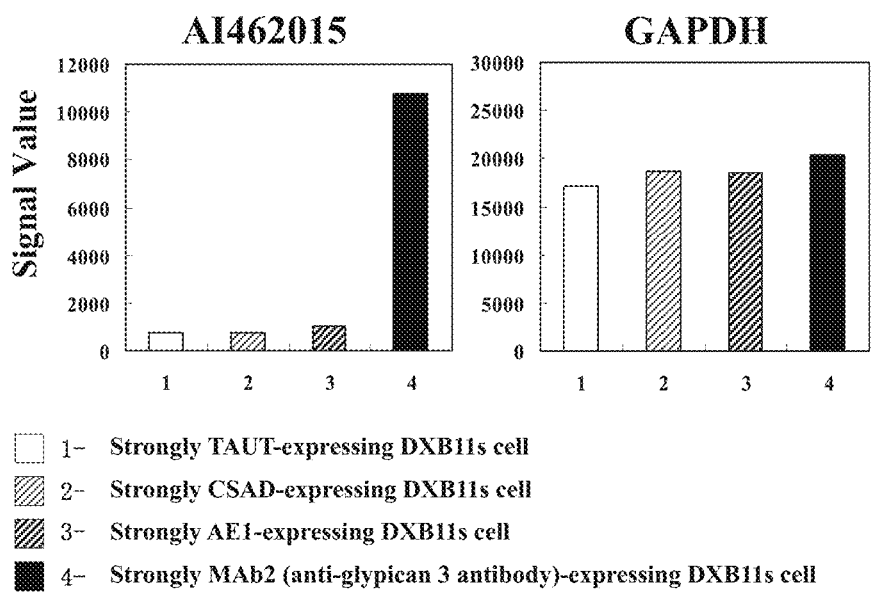
☐ 1− Strongly TAUT-expressing DXB11s cell
▨ 2− Strongly CSAD-expressing DXB11s cell
▨ 3− Strongly AE1-expressing DXB11s cell
■ 4− Strongly MAb2 (anti-glypican 3 antibody)-expressing DXB11s cell
[Figure 4]
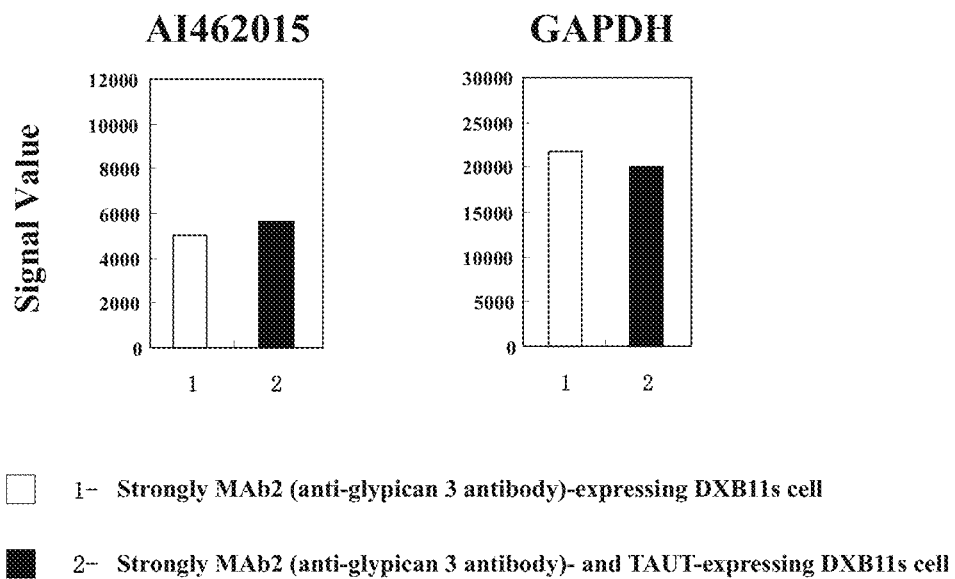
☐ 1− Strongly MAb2 (anti-glypican 3 antibody)-expressing DXB11s cell
■ 2− Strongly MAb2 (anti-glypican 3 antibody)- and TAUT-expressing DXB11s cell

[Figure 5]
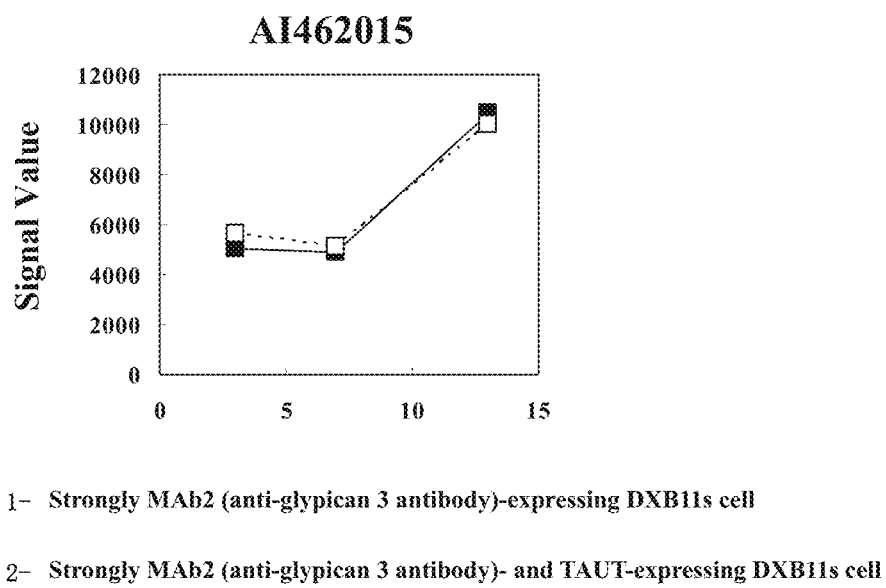
■ 1- Strongly MAb2 (anti-glypican 3 antibody)-expressing DXB11s cell
□ 2- Strongly MAb2 (anti-glypican 3 antibody)- and TAUT-expressing DXB11s cell
[Figure 6]
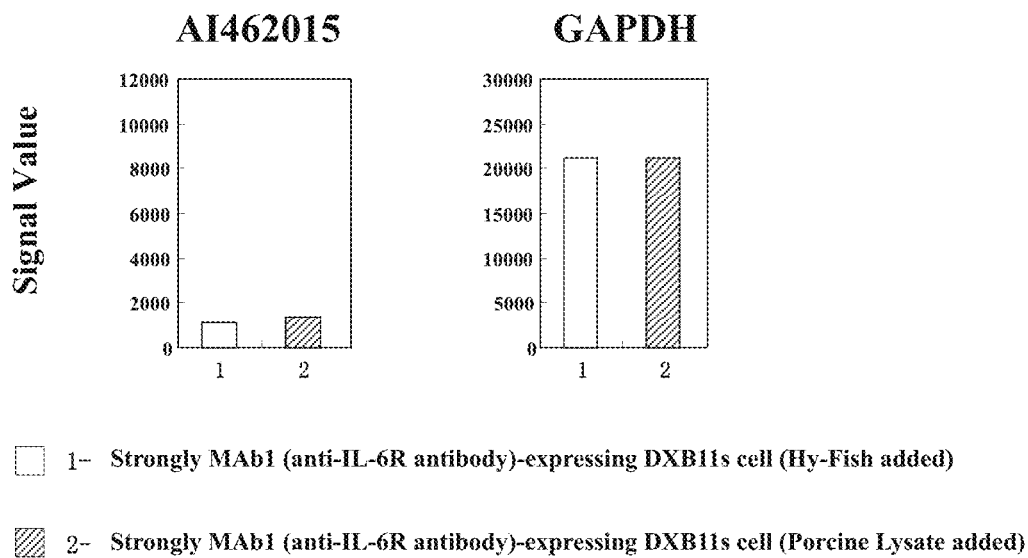
□ 1- Strongly MAb1 (anti-IL-6R antibody)-expressing DXB11s cell (Hy-Fish added)
▨ 2- Strongly MAb1 (anti-IL-6R antibody)-expressing DXB11s cell (Porcine Lysate added)

[Figure 7]
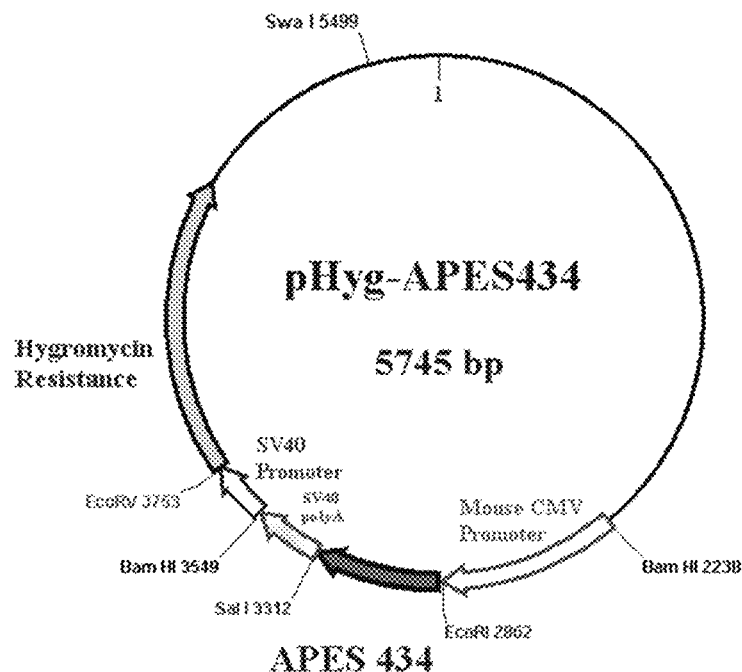
[Figure 8]
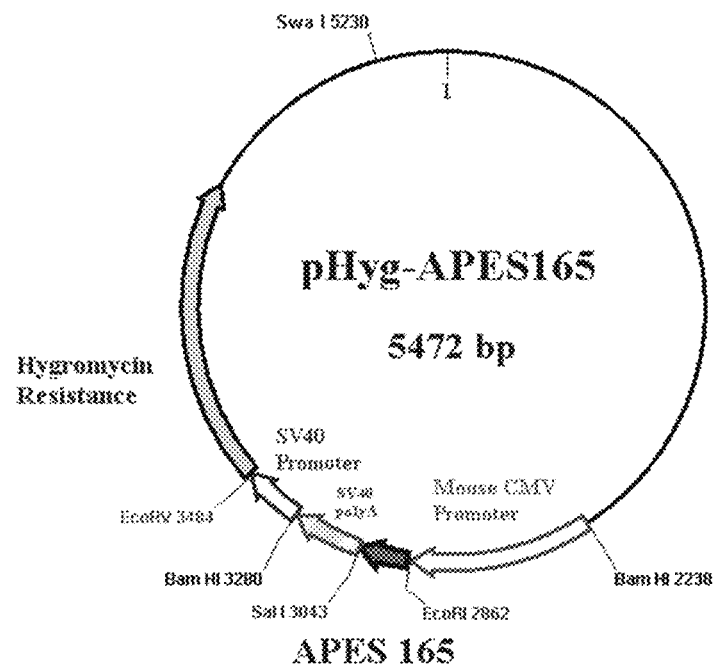

[Figure 9]
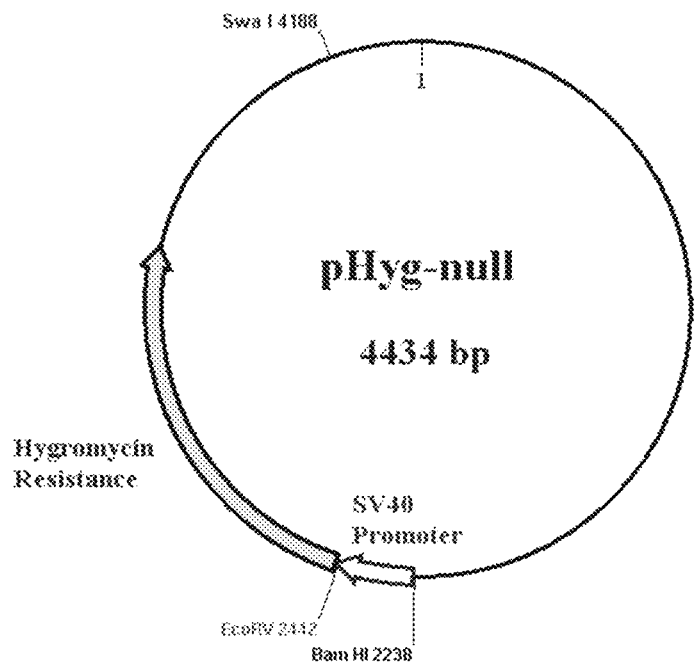
[Figure 10]
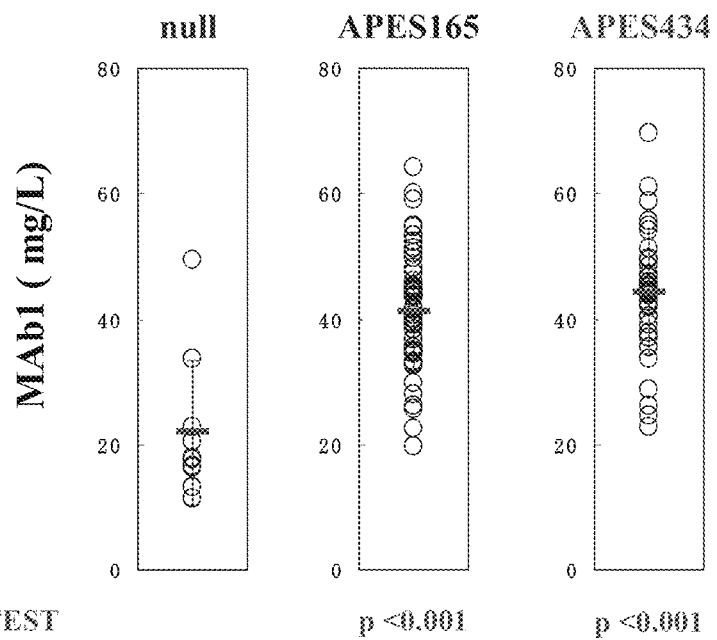

Figure 11

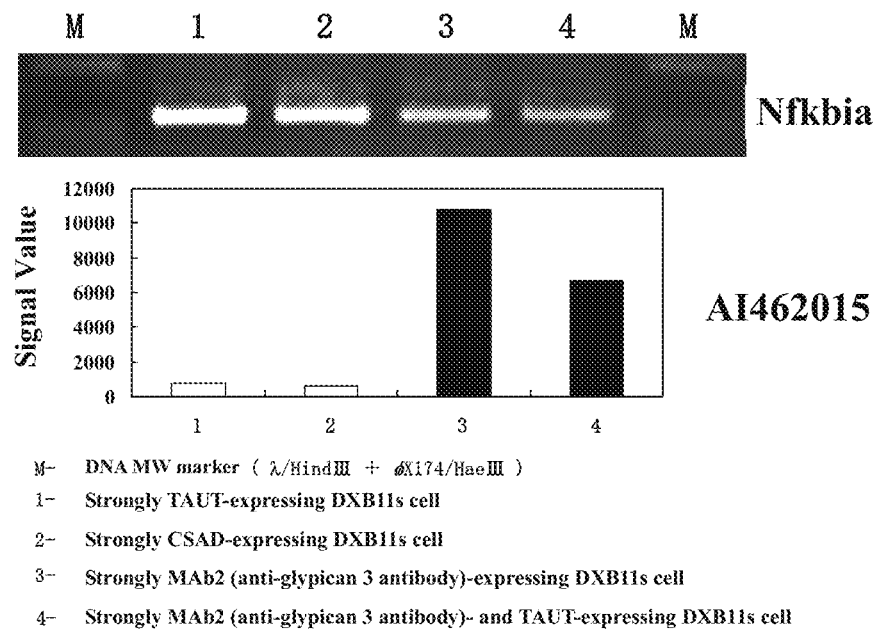

M- DNA MW marker ( λ/HindIII + ϕX174/HaeIII )
1- Strongly TAUT-expressing DXB11s cell
2- Strongly CSAD-expressing DXB11s cell
3- Strongly MAb2 (anti-glypican 3 antibody)-expressing DXB11s cell
4- Strongly MAb2 (anti-glypican 3 antibody)- and TAUT-expressing DXB11s cell

Figure 12

A part of Hamster Nfkbia mRNA (134 bp)

```
         10         20         30         40         50
agtacccggatacagcagcagctgggccagctgacccgggaaaatcttca 60         70         80         90        100
gatgctgcccgagagtgaggatgaggagagctacgacacagagtcagaat 110        120        130
tcacggaggatgagctgccctatgatgactgtgt
```

TaqMan Probe Set for Hamster Nfkbia mRNA

| | | |
|---|---|---|
| 5'- cagctgacccgggaaaatc | Tm 59℃ | 19mer |
| 5'- tgactctgtgtcgtagctctcctc | Tm 59℃ | 24mer |
| 5'- FAM-tcagatgctgcccgagagtgagga-TAMRA | Tm 68℃ | 24mer |

[Figure 13]

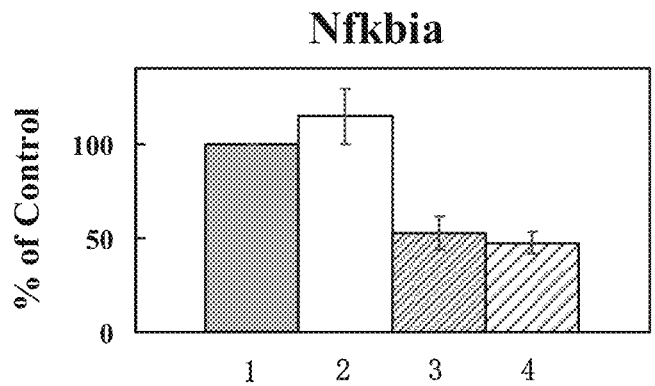

1− Strongly TAUT-expressing DXB11s cell

2− Strongly CSAD-expressing DXB11s cell

3− Strongly MAb2 (anti-glypican 3 antibody)-expressing DXB11s cell

4− Strongly MAb2 (anti-glypican 3 antibody)- and TAUT-expressing DXB11s cell

[Figure 14]

ctctgggctcgaatggcatgggggacagcttttatatggttaactccgcccgttttatgactagaaccaatagttttaatgccaaa
tgcactgaaatcccctaatttgcaaagccaaacgcccctatgtgagtaatacggggacttttacccaattccaagcggaaa
gcccctaatacactcatatggcatatgaatcagcacggtcatgcactctaatggcggcccataggggactttccacataggggg
gcgttcaccatttcccagcataggggtggtgactcaatggccttacccaagtacattgggtcaatgggaggtaagccaatgg
gttttccattactggcaagcacactgagtcaaatgggactttccactggttttgcccaagtacattgggtcaatgggaggtga
gccaatgggaaaaacccattgctgccaagtacactgactcaatagggactttccaatgggttttccattgttggcaagcatata
aggtcaatgtgggtgagtcaatagggactttccattgtatctgcccagtacataaggtcaataggggggtgaatcaacaggaaa
gtcccattggagccaagtacactgcgtcaatagggactttccattgggttttgcccagtacataaggtcaatagggggatgagtc
aatgggaaaaacccattggagccaagtacactgactcaatagggactttccattgggttttgcccagtacatagggtcaatagg
gggtgagtcaacaggaaagttccattggagccaagtacattgagtcaatagggactttccaatgggttttgcccagtacataag
gtcaatgggaggtaagccaatgggttttcccattactggcacgtatactgagtcattagggactttccaatgggttttgcccagt
acataaggtcaatagggggtgaatcaacaggaaagtcccattggagccaagtacactgagtcaatagggactttccattgggttt
tgcccagtacaaaaggtcaatagggggtgagtcaatgggttttccattattggcacgtacataaggtcaatagggggtgagtc
attgggttttccagccaatttaattaaaacgccatgtactttccaccattgacgtcaatgggctattgaaactaatgcaacgtga
cctttaaacggtactttcccatagctgattaatgggaaagtaccgttctcgagccaatacacgtcaatgggaagtgaaagggca
gccaaaacgtaacaccgccccggttttcccctggaaattccatattggcacgcattctattggctgagctgcgttctacgtgggt
ataagaggcgcgaccagcgtcggtaccgtcgcagtcttg

SEQ ID NO: 23

[Figure 15]
Method for Analysis of microRNA Expression
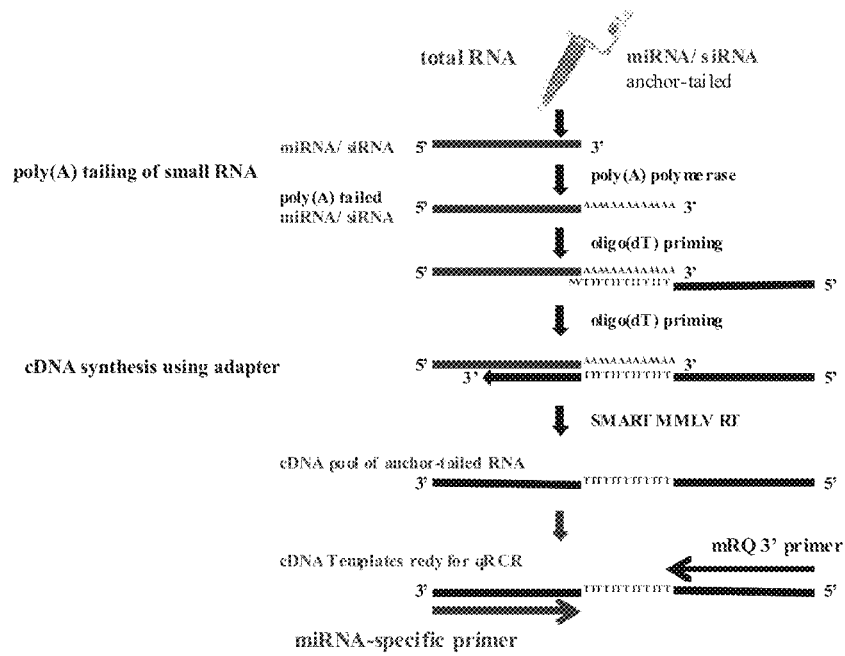
[Figure 16]
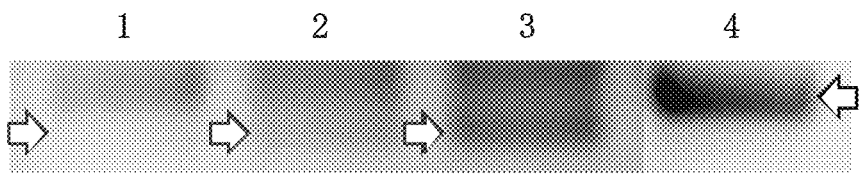
```
1, 2, 3  —  APES 40-61  5' primer / mRQ 3' primer
    4    —  U6 snRNA    5' primer / mRQ 3' primer
    ⇨    —  microRNA (APES 40-61)
    ⇦    —  U6 snRNA
```

[Figure 17]
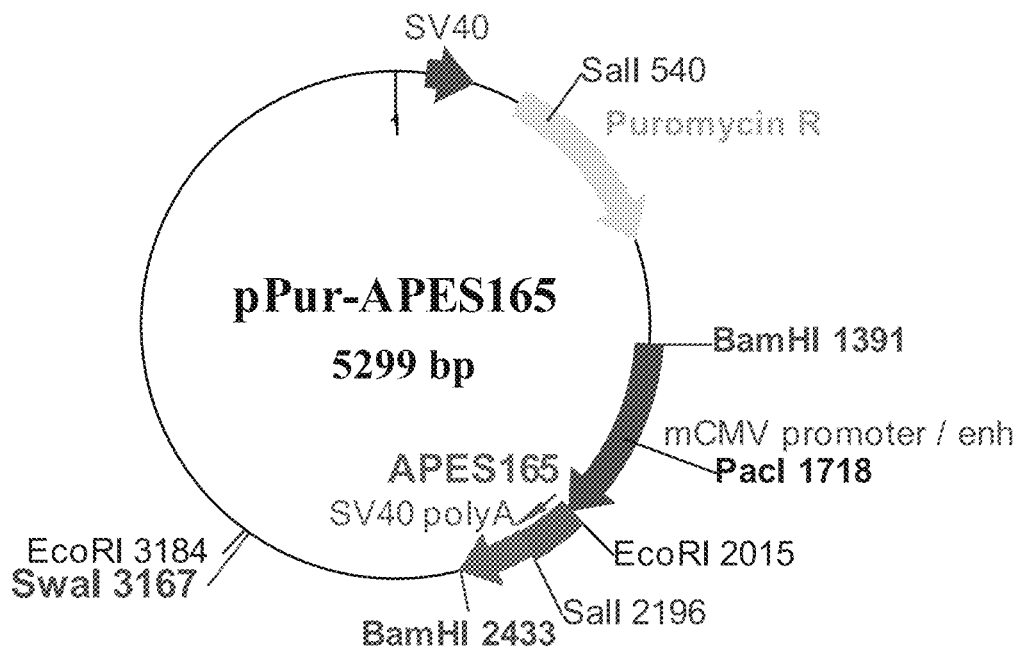
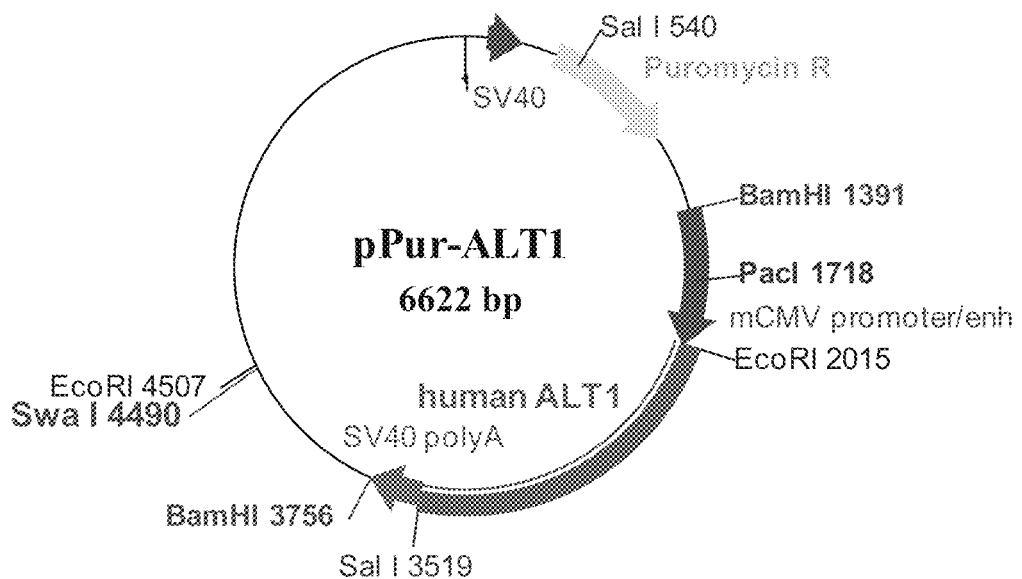

[Figure 18]

| MAb1-producing strain | Highest cell density (x10e6 cells/mL) | Amount of antibody production (g/L/14 days) |
|---|---|---|
| Strongly APES165-expressing strain | 11.5 ±1.7 | 4.4±0.6 |
| Strongly ALT1-expressing strain | 8.9 ±1.8 | 4.0±0.6 |
| Parent strain | 4.1 | 3.4 |

Shaker fed-batch culture (n=3)

[Figure 19]
1L-jar fed-batch culture
- ☐ Strongly APES165-expressing strain  5.3 g/L/12 days  6.0 g/L/14 days
- ○ Strongly ALT1-expressing strain  4.4 g/L/12 days  5.9 g/L/14 days
- ◆ Parent strain  3.2 g/L/12 days  3.9 g/L/14 days
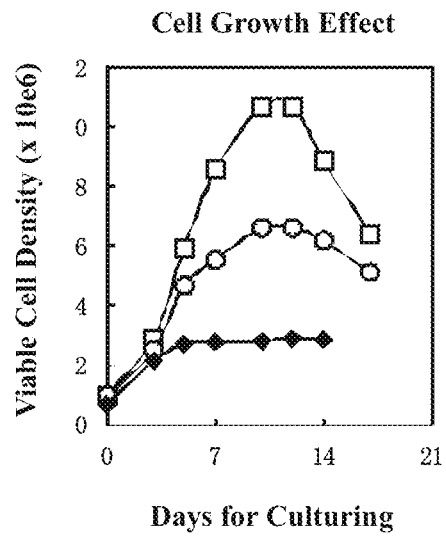
Cell Growth Effect
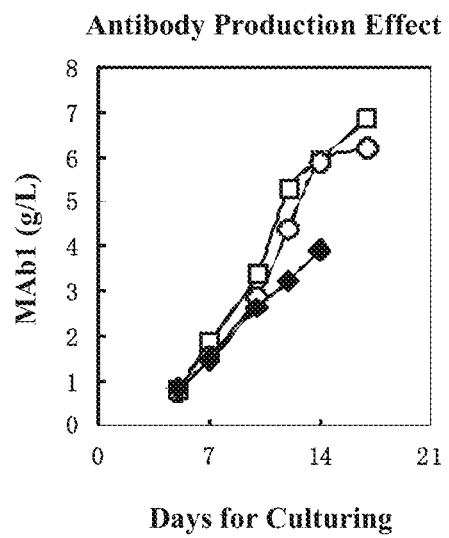
Antibody Production Effect

[Figure 20]
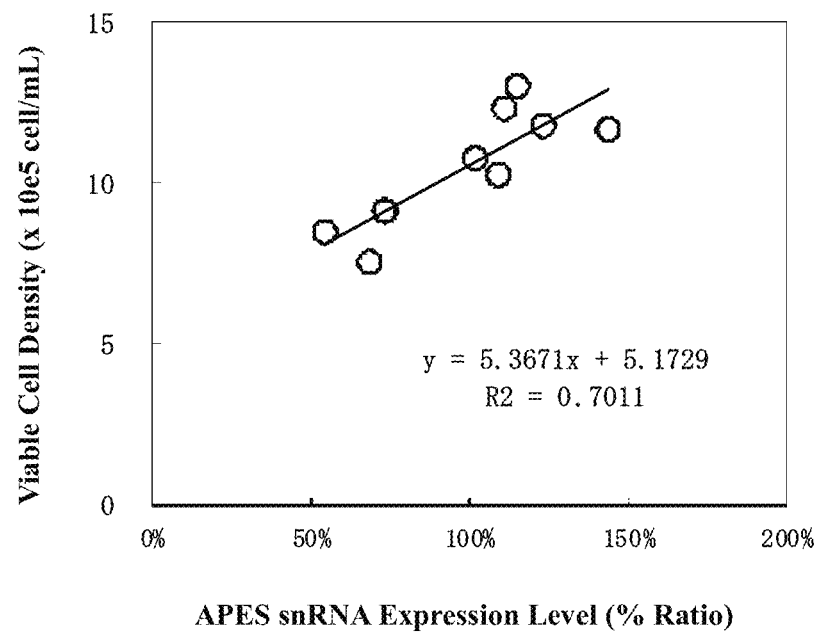
[Figure 21]
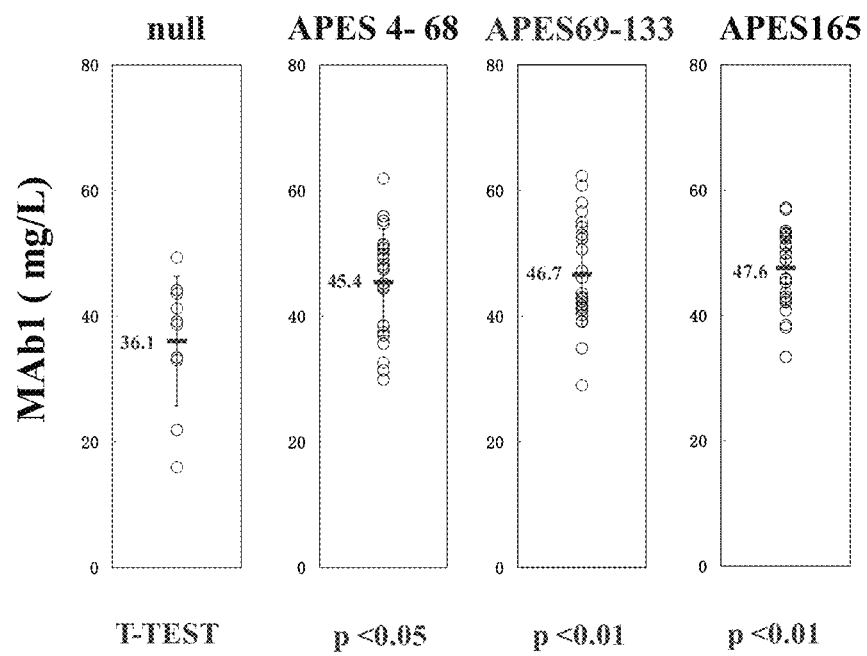

[Figure 24]

```
>gb|...|  Query1 on Cricetulus griseus cell line CHO-K1 unplaced genomic scaffold
scaffold4235, whole genome shotgun sequence Length=486540 Score = 378 bits (418), Expect = 3e-102
Identities = 352/440 (80%), Gaps = 33/440 (7%) Strand=Plus/Minus Query   3      TGTCTGTAAAAATCTGTTTAATAAATATACATCTTAGAAGTACCAAAATAATTACCAACA  62      (AI462015)
               |||||||||||||||||||||||||||||||||||||||||||||||||||||||||||| 
Sbjct   385673 TGTCTGTAAAAATCTGTTTAATAAATATACATCTTAGAAGTACCAAAATAATTACCAACA  385614  (CHO-K1 genome)

Query   63     AAATACAACATATACAACATTTACAAGAAGGCGACACAGACCTTAGTTGGGGGCGACTTT  122     (AI462015)
               ||||||  ||||||||||||||||||  |||  |||| ||| ||| |||| 
Sbjct   385613 AAATACACCATATACAACATTTACAAGAGGGTAACAAAAACCTCAGTCGGGAGTGACT--  385556  (CHO-K1 genome)

Query   123    TAAGCACATGCCACTGAACACCTGGCTCTTACATGGGAGGACACACTGGGCTCACTTACT  182     (AI462015)
               ||||||  ||||  |||||||||  ||  |||||  |||||| ||  ||||  ||| ||| 
Sbjct   385555  --AGCACATACCACTCAACACCTGGTTC-TACATGTGAGGACATACCAGGCTCAGCTACC  385499  (CHO-K1 genome)

Query   183    AGGTCTATGGTGGTTCAATCAAAAGCACAATAAATAAAACGTGGT-CCTTTCATTAGGTT  241     (AI462015)
               ||  ||||  ||||||||||||||||||||||||  |||||  ||||||| | | 
Sbjct   385498 AGATCTA----CCGTTCAGTCAAAAGCACAATAAATAGAATGTGGTCCCTTTCATCAG--T  385444  (CHO-K1 genome)

Query   242    CTGGAAAATCACCTccccccccccaaaaaaaaTCCCACAAACATGAACCTTAAGAGACA  301     (AI462015)
               ||||||| |||||||||  |  |||  |||  |  |||| |||||
Sbjct   385443 CTGGAAAACCACCTCCC--------------AAAACCTCACGAATGTGAGCTTTAAAAGACA  385396  (CHO-K1 genome)

Query   302    TTTTCTTTGAATTTCAGTGATCTGTTTCCCCGGATTTCACAAAGACAACA----GCCGAA  357     (AI462015)
               |||||||||||||  |||||||||||||||  |||||||||||||  |||||  |
Sbjct   385395 TTTTCTTTGAATTCCAATGATCTGTTTCCCC--ATTTCACAAAAATAACAATCTGCC---A  385340  (CHO-K1 genome)

Query   358    TCACCCCAGTAAAATGCCTGGGTCTAGGCGCTGTGTGGTGTGGTGCTAAGTATA-CCCTT  416     (AI462015)
               ||||  |||| |||  ||||  |||| ||||  ||||||||  ||||||||| |||| 
Sbjct   385339 TCACCAGAGTAAGATGCTTGGGGGCAGGCTGTGTGCAGTGTGGTGGTAAGTATATCCCTT  385280  (CHO-K1 genome)

Query   417    TC-TCAttttttttcttttt  435
               || |  |||||||||||| ||
Sbjct   385279 TCTTTCTTTTTTTTCTTCTT  385260
```

SEQ ID NO: 40

[Figure 25a]

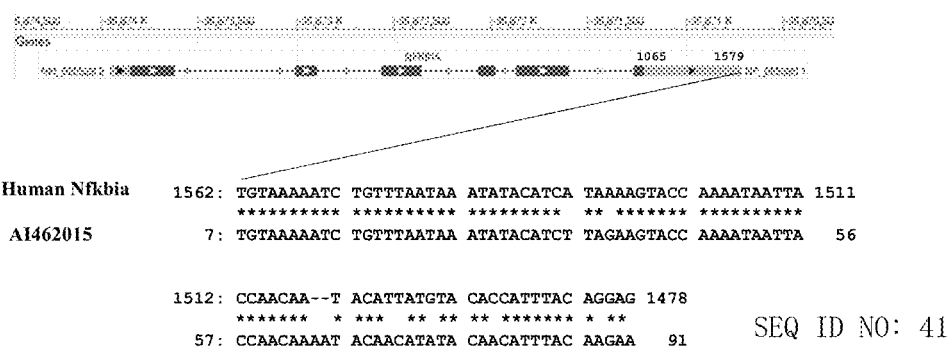

```
Human Nfkbia   1562: TGTAAAAATC TGTTTAATAA ATATACATCA TAAAAGTACC AAAATAATTA  1511
                    ********** ********** ********  ** ******* **********
AI462015          7: TGTAAAAATC TGTTTAATAA ATATACATCT TAGAAGTACC AAAATAATTA    56

1512: CCAACAA--T ACATTATGTA CACCATTTAC AGGAG  1478
                    *******  * *** ** ** ** ******* * **
                 57: CCAACAAAAT ACAACATATA CAACATTTAC AAGAA    91
```

SEQ ID NO: 41

Matching = 75/85 (88%)

[Figure 25b]

```
Rat Nfkbia    1562: TGTAAAAATC TGTTTAATAA ATATACATCT TAGAAGTACC AAAATAATTA 1511
                   ********** ********** ********** ********** **********
AI462015         7: TGTAAAAATC TGTTTAATAA ATATACATCT TAGAAGTACC AAAATAATTA   56

1512: CCAACAAAAT ACACCATATA CAACATTTAC AAGAA 1478
                   ********** *** ****** ********** *****
                57: CCAACAAAAT ACAACATATA CAACATTTAC AAGAA   91
```

Matching = 84/85 (99%)

SEQ ID NO: 42

[Figure 25c]

```
Chimpanzee Nfkbia  2209: TGTAAAAATC TGTTTAATAA ATATACATCA TAAAAGTACC AAAATAATTA 2158
                        ********** ********** ********  ** ****** **********
AI462015              7: TGTAAAAATC TGTTTAATAA ATATACATCT TAGAAGTACC AAAATAATTA   56

2159: CTAAC--AAT ACATTATGTA CATCATTTAC AGGAGGGTAA C 2121
                        * ***  *** *** ** ** ** ******* *  **     *
                     57: CCAACAAAAT ACAACATATA CAACATTTAC A--AG----A A   91
```

Matching = 75/85 (88%)

SEQ ID NO: 43

[Figure 25d]

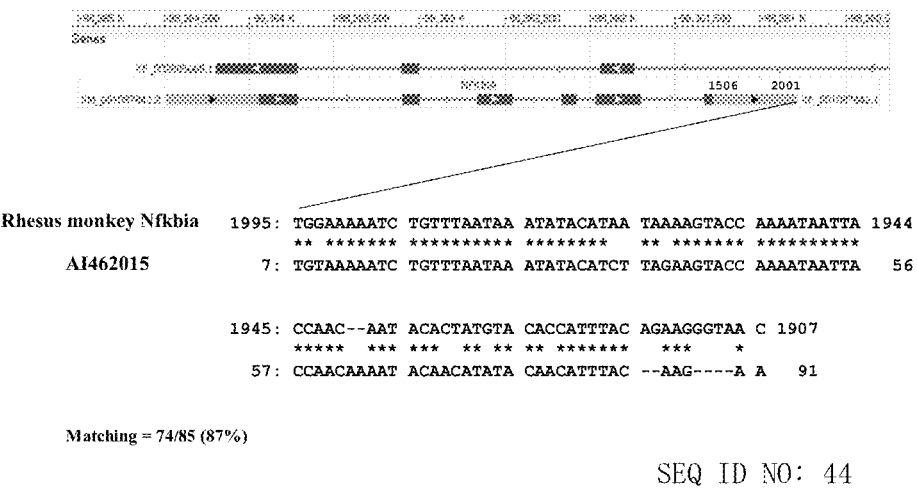

| | | | | | | |
|---|---|---|---|---|---|---|
|Rhesus monkey Nfkbia|1995:|TGGAAAAATC|TGTTTAATAA|ATATACATAA|TAAAAGTACC|AAAATAATTA 1944|
| | |** *******|**********|*******|** *******|**********|
|AI462015|7:|TGTAAAAATC|TGTTTAATAA|ATATACATCT|TAGAAGTACC|AAAATAATTA   56|

```
1945: CCAAC--AAT ACACTATGTA CACCATTTAC AGAAGGGTAA C 1907
      ***** *** *** ** ** ** *******  ***   *
  57: CCAACAAAAT ACAACATATA CAACATTTAC --AAG----A A   91
```

Matching = 74/85 (87%)

SEQ ID NO: 44

[Figure 25e]

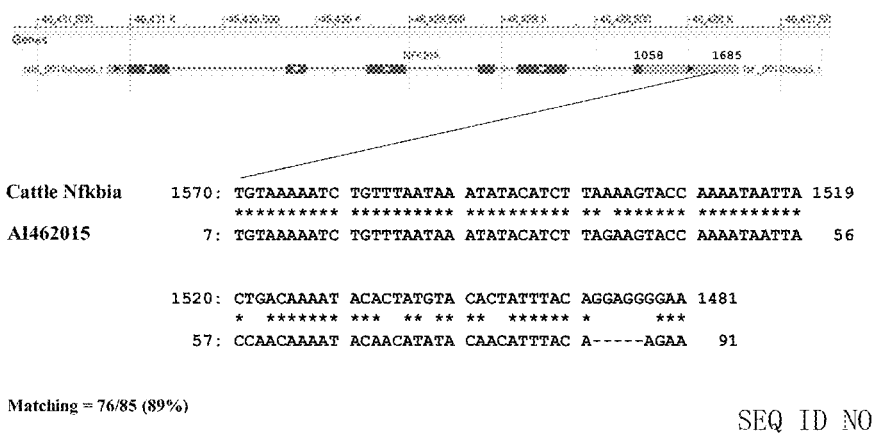

| | | | | | | |
|---|---|---|---|---|---|---|
|Cattle Nfkbia|1570:|TGTAAAAATC|TGTTTAATAA|ATATACATCT|TAAAAGTACC|AAAATAATTA 1519|
| | |**********|**********|**********|** *******|**********|
|AI462015|7:|TGTAAAAATC|TGTTTAATAA|ATATACATCT|TAGAAGTACC|AAAATAATTA   56|

```
1520: CTGACAAAAT ACACTATGTA CACTATTTAC AGGAGGGGAA 1481
      * ******* *** ** ** ** ****** *    ***
  57: CCAACAAAAT ACAACATATA CAACATTTAC A-----AGAA   91
```

Matching = 76/85 (89%)

SEQ ID NO: 45

RECOMBINANT POLYPEPTIDE PRODUCTION METHOD

SEQUENCE LISTING

The instant application contains a Sequence Listing which has been submitted electronically in ASCII format and is hereby incorporated by reference in its entirety. Said ASCII copy, created on Mar. 23, 2015, is named 060641-0130_SL.txt and is 17,533 bytes in size.

CROSS-REFERENCE TO RELATED APPLICATIONS

This application is a National Stage application of PCT/JP2012/058577, filed Mar. 30, 2012, which claims priority from Japanese application JP2011-082002, filed Apr. 1, 2011.

The instant application contains a Sequence Listing which has been submitted in ASCII format via EFS-WEB and is herby incorporated by reference in its entirety. Said ASCII copy, created on Sep. 25, 2013, is named sequence.txt and is 12 KB.

TECHNICAL FIELD

The present invention relates to a method of producing a recombinant polypeptide, and more specifically, to a method of producing a polypeptide efficiently using an animal cell in which the expression of nuclear factor κB inhibitor α (NfkBia) has been decreased.

BACKGROUND ART

When proteins useful as medicaments are produced using gene recombination technology, use of animal cells enables complicated post-translational modification and folding which prokaryotic cells cannot perform. Hence, animal cells have been frequently used as host cells for producing recombinant proteins.

In recent years, a large number of biopharmaceuticals such as antibodies and physiologically active proteins have been developed. Techniques that permit recombinant proteins to be produced efficiently by animal cells lead to cost reduction of biopharmaceuticals and promise their stable supply to patients.

Under these circumstances, a method of protein production with higher production efficiency is desired.

NfkBia (IKBα, nuclear factor κB inhibitor α), which is an abbreviation of nuclear factor of kappa light polypeptide gene enhancer in B-cells inhibitor, alpha, is involved in activation of NF-kappa B, a transcription factor related to intracellular signaling. NfkBia is one of factors that inactivate NF-kappa B. The inducible nuclear expression of newly biosynthesized NfkBia negatively regulates the DNA binding and transcriptional activities of NF-kappa B (Non-Patent Document 1). Further, the expression of some genes that inhibit cell proliferation, like NfkBia, is suppressed in almost all mouse or human tumor cells (Non-Patent Document 2). NF-kappa B usually exists in a state where it is bound to an inactivator such as NfkBia. When various stimulations are given, NF-kappa B is released from such an inactivator, activated and translocated into the nucleus, and binds to a specific DNA sequence in the promoter/enhancer regions of various target genes of cytokine, growth factors, adhesion molecules, cell death regulators, and the like (5'-GGGACTTTCC-3'; the DNA sequence is called NFκB-binding sequence, kB motif, NFkB response element, or the like (SEQ ID NO: 35)), and NF-kappa B is thus involved in modulating transcriptional activities (Non-Patent Document 3).

Meanwhile, it has been totally unknown how NfkBia is related to the recombinant protein-producing ability, as a behavior of NfkBia within cultured animal cells.

CITATION LIST

Non Patent Literature

Non-Patent Document 1: Inducible nuclear expression of newly synthesized I kappa B alpha negatively regulates DNA-binding and transcriptional activities of NF-kappa B, Mol. Cell. Biol., May 1995, 2689-2696, Vol. 15, No. 5

Non-Patent Document 2: From mice to humans: Identification of commonly deregulated genes in mammary cancer via comparative SAGE studies, Hu Y., Sun H., Drake J., Kittrell F., Abba M. C, Deng L., Gaddis S., Sahin A., Baggerly K., Medina D. and Aldaz C. M., Cancer Research 2004 64:21 (7748-7755)

Non-Patent Document 3: "New insights into the Role of Nuclear Factor-kappa B in Cell Growth Regulation", American Journal of Pathology, 2001, Vol. 159, No. 2: 387-397

SUMMARY OF INVENTION

Technical Problem

It is an object of the present invention to provide a method capable of producing a natural or recombinant protein at a high level.

Solution to Problem

The present inventors used cultured cell strains (CHO cell strains) having high recombinant antibody-producing ability to conduct studies on genes expressed markedly in the cell strains, in diligent efforts to achieve the above object. As a result, the present inventors identified one mRNA type non-coding RNA that was recognized by using a specific mouse sequence as a probe. This transcript corresponded to the complementary strand of the untranslated region of NfkBia mRNA. Further, the present inventors found that expressing in cultured recombinant cells a nucleic acid molecule consisting of a partial sequence of the transcript markedly increases the recombinant polypeptide-producing ability of the cultured cells. The present inventors also found that NfkBia expression was suppressed in the highly antibody-producing cells in which the non-coding RNA expression had been increased. The present inventors further found that the cultured cells having the high recombinant antibody-producing ability suppressed the NfkBia expression in the cells. Based on these findings, the present inventors expected that the production amount of a desired polypeptide would be able to be increased by inducing high expression of a transcript that regulates the NfkBia expression in cultured cells. These findings led to the completion of the present invention.

Such an RNA or DNA or sequence thereof that has the function of increasing the ability to produce a protein such as a recombinant antibody by increased expression of itself in cultured cells is collectively named herein as APES (Antibody Production Enhancing Sequence) (also referred to as PPES (Polypeptide Production Enhancing Sequence) in some cases).

The present inventors presumed that APES (or PPES) would regulate the NfkBia expression in cultured cells, thereby enhancing the activity of Nf-kappa B and thus increasing the recombinant polypeptide-producing ability. It is presumed that the NF-kappa B having enhanced activity would be translocated into the nucleus, increase the expression of genes related to immunity, inflammation and anti-apoptosis (e.g., Bcl-2, Bcl-xL, IAPs (Inhibitors of Apoptosis Proteins)) and contribute to the growth of the cells, the maintenance of the survival rate of the cells, and the like.

Furthermore, a plurality of NF-kappa B-binding sequences exist in the promoter/enhancer regions of common plasmids for expression of a gene encoding a recombinant protein or peptide such as an antibody. Hence, it is also presumed that NF-kappa B that has been translocated into the nucleus would enhance the promoter activity of the expression plasmids and contribute to higher antibody production. For example, in the case of the MCMV promoter, such NF-kappa B-binding sequences exist at eight sites in a mouse cytomegalovirus-derived sequence (DD434486) and at three sites in a human cytomegalovirus-derived sequence (DI097553).

The present invention is summarized as follows:
(1) A method of producing a polypeptide comprising culturing a cell that expresses APES and into which a DNA encoding a desired polypeptide has been introduced, thereby producing the desired polypeptide.
(1-1) The method according to (1), wherein the cell is a strongly APES-expressing cell.
(2) The method according to (1), wherein the APES is a nucleic acid molecule comprising a nucleotide sequence that can bind to the DNA or mRNA of NfkBia gene derived from human, mouse, rat or hamster by base pairing and thereby can suppress the expression of the NfkBia gene.
(3) The method according to (2), wherein the APES is a small RNA of at most 30 nucleotides in length comprising a sequence of 19 to 25 nucleotides in length that can bind to a part of the NfkBia mRNA by base pairing.
(4-1) The method according to (2), wherein the APES is an mRNA type non-coding RNA of at most 561 nucleotides in length comprising a sequence of 19 to 25 nucleotides in length that can bind to a part of the NfkBia mRNA by base pairing.
(4) The method according to (2), wherein the APES is an mRNA type non-coding RNA of at most 500 nucleotides in length comprising a sequence of 19 to 25 nucleotides in length that can bind to a part of the NfkBia mRNA by base pairing.
(5-1) The method according to (2), wherein the APES is an mRNA type non-coding RNA of 561 to 1579 nucleotides in length comprising a sequence of 19 to 25 nucleotides in length that can bind to a part of the NfkBia mRNA by base pairing.
(5) The method according to (2), wherein the APES is an mRNA type non-coding RNA of 500 to 1000 nucleotides in length comprising a sequence of 19 to 25 nucleotides in length that can bind to a part of the NfkBia mRNA by base pairing.
(6) The method according to any of (3) to (5), wherein the continuous sequence of 19 to 25 nucleotides in length is any partial sequence in the nucleotide sequence represented by SEQ ID NO: 2.
(7-1) The method according to (6), wherein the APES is selected from nucleic acid molecules each comprising any of the following nucleotide sequences:
(a) a DNA consisting of the nucleotide sequence of any of SEQ ID NOs:1 to 16 and 29;
(b) a DNA that comprises the sequence of (a) above and is a partial sequence of the 3' untranslated region of the NfkBia gene;
(c) a DNA consisting of the nucleotide sequence identical to the sequence of (a) or (b) above except for one or several nucleotides;
(d) an RNA that is a transcript of (a), (b) or (c) above; and
(e) a DNA or RNA consisting of the sequence that can bind to the sequence of (a) above by base pairing.
(7) The method according to (6), wherein the APES is selected from nucleic acid molecules each comprising any of the following nucleotide sequences:
(a) a DNA consisting of the nucleotide sequence of any of SEQ ID NOs: 4 to 16;
(b) an RNA that is a transcript of (a) above;
(c) a DNA consisting of the nucleotide sequence identical to the sequence of (a) above except for one nucleotide;
(d) an RNA that is a transcript of (c) above; and
(e) a DNA or RNA consisting of the sequence that can bind to the sequence of (a) above by base pairing.
(8) The method according to (1), wherein an exogenous DNA encoding the desired polypeptide has been introduced into the cell and the APES has been artificially introduced into the cell.
(9) The method according to (8), wherein the cell into which the APES has been artificially introduced is a cell transfected with the APES.
(10) The method according to (8), wherein the cell into which the APES has been artificially introduced is a cell in which the transcription of endogenous APES has been activated.
(11) The method according to (8), wherein a DNA encoding a taurine transporter has been further introduced into the cell.
(12) The method according to (8), wherein a DNA encoding cysteine sulfinic acid decarboxylase has been further introduced into the cell.
(13) The method according to (8), wherein a DNA encoding alanine transferase has been further introduced into the cell.
(14) The method according to (1), wherein the polypeptide is an antibody.
(15) The method according to (1), wherein the cell is a Chinese hamster ovary cell.
(16) A method of producing a pharmaceutical comprising the polypeptide produced by any of the methods shown above.
(17) A nucleic acid molecule (APES or PPES) that comprises any of the following nucleotide sequences and has APES activity, provided that the nucleic acid molecule of SEQ ID NO: 1 is excluded:
(a) a DNA consisting of the nucleotide sequence of any of SEQ ID NOs: 2 to 16 and 29;
(b) a DNA that comprises the sequence of (a) above and is a partial sequence of the 3' untranslated region of NfkBia gene;
(c) a DNA consisting of the nucleotide sequence identical to the sequence of any of SEQ ID NOs: 1 to 16 and 29 or the sequence of (b), except for one or several nucleotides;

(d) an RNA that is a transcript of (a), (b) or (b) above; or
(e) a DNA or RNA consisting of the sequence that can bind to the sequence of (a) above by base pairing.
(18) A vector comprising the nucleic acid molecule according to (17) above.
(19) A cell into which the nucleic acid molecule according to (17) above or the vector according to (18) above has been artificially introduced.

Advantageous Effects of Invention

The present invention enables the efficient production of recombinant proteins.

BRIEF DESCRIPTION OF DRAWINGS

FIG. 1 shows the sequence of the identified AI462015 transcript and its location on mouse genome. Figure discloses SEQ ID NOS 10 and 1, respectively, in order of appearance.

FIG. 2 shows the expression intensity of the AI462015 transcript on the 3rd day of a subculture of an antibody-producing cell obtained by expressing Mab1 (anti-IL-6 receptor antibody) at a high level in a CHO-DG44 cell.

FIG. 3 shows the expression intensity of the AI462015 transcript on the 3rd day of a subculture of an antibody-producing cell obtained by expressing Mab2 (anti-glypican 3 antibody) at a high level in a CHO-DXB11s cell.

FIG. 4 shows the expression intensity of the AI462015 transcript on the 3rd day of a 1L-jar fed-batch culture of Mab2 (anti-glypican 3 antibody)-producing cells.

FIG. 5 shows an increase of the expression intensity of the AI462015 transcript on the 13th day at the late stage of the 1L-jar fed-batch culture of the Mab2-producing cells.

FIG. 6 shows the expression intensity of the AI462015 transcript on the 3rd day of a 1L-jar fed-batch culture of cells that had low potential to produce Mab1 (anti-IL-6 receptor antibody).

FIG. 7 shows an expression plasmid of a partial sequence 434 bp of the transcript AI462015 (437p).

FIG. 8 shows an expression plasmid of a partial sequence 165 bp of the transcript AI462015 (437p).

FIG. 9 shows a plasmid in which only a hygromycin resistance gene was expressed as a control.

FIG. 10 shows that the amount of Mab1 production is increased by the strong expression of partial sequences of the transcript AI462015 (437p).

FIG. 11 shows the strong expression of the transcript AI462015 and the suppressed NfkBia expression in highly antibody-producing cells.

FIG. 12 shows a probe set used to quantify the NfkBia expression. FIG. 12 depicts a part of hamster NfkBia mRNA (134 bp) (SEQ ID NO: 36), and a TAQMAN® probe set (SEQ ID NOs: 20-22).

FIG. 13 shows a result of the quantification of the suppressed NfkBia expression in the highly antibody-producing cells.

FIG. 14 shows the eight NfkB-binding sites on the mouse CMV IE2 promoter (SEQ ID NO: 23) (the sites are underlined).

FIG. 15 is an outline of a method for analysis of microRNA expression. Figure discloses SEQ ID NOS 46, 46-47, 46, 48, 48 and 48, respectively, in order of appearance.

FIG. 16 shows PCR products derived from microRNAs that had been expressed at high levels in highly antibody-producing cells.

FIG. 17 shows plasmids pPur-APES165 and pPur-ALT1 that were used for co-expression of the partial sequence 165 bp of the transcript AI642048 (437p) and co-expression of ALT1, respectively, in pHyg-TAUT-expressing cells.

FIG. 18 shows a result of a shaker fed-batch culture that shows a high cell growth effect and high antibody production effect that resulted from the strong expression of APES.

FIG. 19 shows a result of a 1L-jar fed-batch culture that shows a high cell growth effect and high antibody production effect that resulted from the strong expression of APES.

FIG. 20 shows a correlation between the APES expression level of strongly APES165-expressing candidate host cells (nine strains) and their viable cell density.

FIG. 21 shows that the amount of Mab1 production is increased by the strong expression of partial sequences of the partial sequence APES165 of the transcript AI462015 (437p).

FIG. 22 depicts sequences of 5'-GAATTC-CGCC-3' (SEQ ID NO: 37) and 5'-ATTATC-CAGCTG-3' (SEQ ID NO: 38).

FIG. 24 shows that there is a homologous sequence of AI462015 on CHO-K1 cell genome (Example 8) (SEQ ID NO: 40). Figure discloses the "Sbjct" sequence as SEQ ID NO: 26.

FIG. 25a shows that a partial sequence (nucleotides 7 to 91 from the 5' end) of AI462015 (SEQ ID NO: 29) is conserved regardless of species (SEQ ID NO: 41).

FIG. 25b shows that a partial sequence (nucleotides 7 to 91 from the 5' end) of AI462015 (SEQ ID NO: 29) is conserved regardless of species (SEQ ID NO: 42).

FIG. 25c shows that a partial sequence (nucleotides 7 to 91 from the 5' end) of AI462015 (SEQ ID NO: 29) is conserved regardless of species (SEQ ID NO: 43).

FIG. 25d shows that a partial sequence (nucleotides 7 to 91 from the 5' end) of AI462015 (SEQ ID NO: 29) is conserved regardless of species (SEQ ID NO: 44).

FIG. 25e shows that a partial sequence (nucleotides 7 to 91 from the 5' end) of AI462015 (SEQ ID NO: 29) is conserved regardless of species (SEQ ID NO: 45).

DESCRIPTION OF EMBODIMENTS

Figure 22:
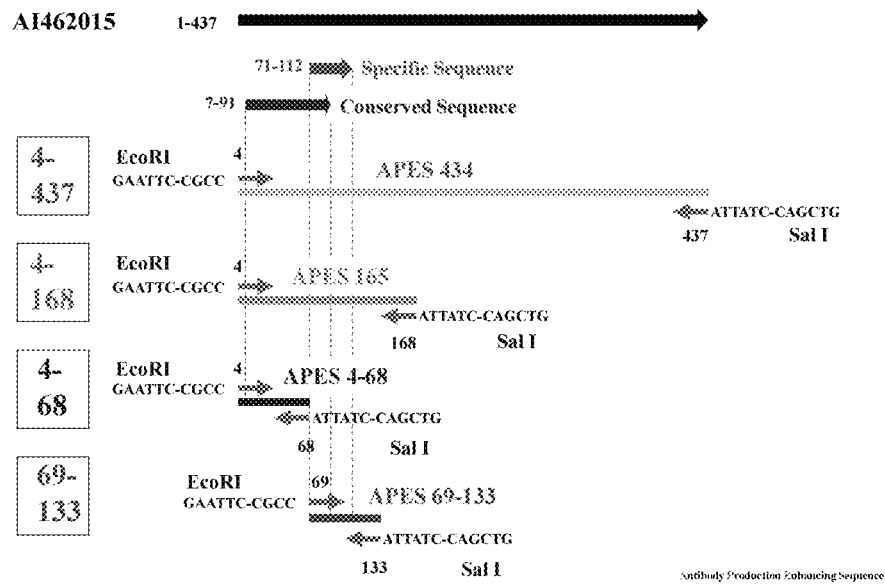
FIG. 22 shows that the partial sequences of APES165, which were found to have a high antibody production effect as shown in FIG. 21, comprise the Nfkbia complementary sequence.

Embodiments of the present invention are described below in more detail.

(1) APES (Antibody Production Enhancing Sequence)

The present invention provides a method of producing a polypeptide comprising culturing a cell that expresses APES and into which a DNA encoding a desired polypeptide has been introduced, thereby producing the desired polypeptide.

As detailed in the Examples described later, the present inventors found an mRNA type non-coding RNA with an increased expression level correlated with the antibody-producing ability in cultured CHO cells, and the present inventors identified the mRNA type non-coding RNA as a transcript of 437 nucleotides in mouse genome (FIG. 1; GenBank Accession ID: AI462015; SEQ ID NO: 1). The sequence of AI462015 and its location on mouse genome are shown in FIG. 1. The AI462015 sequence exists on the complementary strand near the 3' untranslated region of NfkBia (nuclear factor κB inhibitor α) mRNA on mouse genome (Note: The subsequent information update given by GeneBank revealed that the 437-nucleotide transcript of AI462015 corresponds to the complementary strand of the 3' untranslated region (513 nucleotides) of mouse NfkBia mRNA (FIG. 23)).

Further, the present inventors found that the production amount of the desired polypeptide can be increased by introducing nucleic acid molecules each having an AI462015-derived partial sequence into host cells to thereby enable the expression.

The present inventors presumed that these nucleic acid molecules would regulate the NfkBia expression in cultured cells, thereby enhancing the activity of Nf-kappa B and thus increasing the recombinant polypeptide-producing ability. Specifically, the present inventors presumed that the NF-kappa B having enhanced activity would be translocated into the nucleus, increase the expression of genes related to immunity, inflammation and anti-apoptosis (e.g., Bcl-2, Bcl-xL, IAPs (Inhibitors of Apoptosis Proteins)) and contribute to the growth of the cells, the maintenance of the survival rate of the cells, and the like.

The present inventors collectively named as APES (Antibody Production Enhancing Sequence) (also referred to as PPES (Polypeptide Production Enhancing Sequence) in some cases) an RNA or DNA or sequence thereof which has the following functions provided by its own expression or increased expression in cultured cells: regulating the NfkBia expression in the cultured cells and thereby enhancing the activity of Nf-kappa B and increasing the ability to produce a desired recombinant polypeptide such as a recombinant antibody, and which preferably does not encode proteins.

The foregoing AI462015-derived sequence or a partial sequence thereof is conserved in not only rodents such as mouse and hamster but also human, and is deemed to be also a highly conserved sequence in other mammals and animals such as fish and insects. Hence, a partial sequence of the 3' untranslated region of various animal cell-derived NfkBia mRNA or sequence complementary to the sequence (the partial sequence and the complementary sequence correspond to the AI462015-derived sequence or partial sequence thereof) also can be used as the APES sequences of the present invention.

In one embodiment, a part of the APES sequence comprises the Nfkbia complementary sequence or is the Nfkbia complementary sequence, and this feature results in the suppression of the Nfkbia expression in APES-expressing cells. This suppression effect promotes the function of producing an antibody and the like at high levels.

In one embodiment, APES is a nucleic acid molecule that interferes with NfkBia mRNA (RNA interference) and that has the function of binding itself to NfkBia mRNA in a cell to negatively regulate the mRNA expression. The increase of the intracellular expression level of APES leads to the suppressed expression of the NfkBia function and thereby increases the expression level of antibody genes and further produces a recombinant polypeptide such as an antibody at high levels.

Thus, APES can be the following one comprising a sequence that can bind to the DNA or mRNA of the NfkBia gene by base pairing: a double-stranded RNA (dsRNA) or an siRNA, which is a short dsRNA, or an siRNA dissociated into single strands, or an shRNA. an antisense DNA or RNA, a microRNA (miRNA) or an mRNA type non-coding RNA.

For example, the APES sequence can be an oligonucleotide consisting of a sequence comprising a partial sequence complementary to target NfkBia mRNA. Such an oligonucleotide is, for example, a miRNA that has a sequence corresponding to 19 to 25 nucleotides in the complementary strand of NfkBia mRNA or a sequence identical to the above sequence except for one nucleotide and that has the effect to suppress the NfkBia expression. Alternatively, APES may be a long chain, mRNA type non-coding RNA and can be, for example, such an RNA that consists of a sequence of 561 nucleotides in length (561 mer) or at most 500 nucleotides in length (500 mer) comprising a sequence capable of binding to the DNA or mRNA of the NfkBia gene by base pairing and that has the effect to suppress the NfkBia expression. Alternatively, APES may be a longer chain (hundreds to hundreds of thousands of nucleotides), mRNA type non-coding RNA. For example, APES can be a nucleic acid molecule or sequence of 200 to 100000 nucleotides in length or 300 to 300000 nucleotides in length.

The sequence that can bind by base pairing is not limited to a completely pairing sequence (i.e., a 100% complementary sequence), but the presence of non-pairing nucleotides is also acceptable as long as they do not interfere with its functions. Rather, partial complementation is preferred depending on the form of APES. Hence, for example, a sequence that is at least 70%, more preferably 80%, still more preferably 90%, most preferably 95% homologous to a genetic DNA or mRNA comprising the NfkBia untranslated region, or the sequence complementary to the above sequence is also encompassed in the "sequence that can bind by base pairing". For example, as for an mRNA type non-coding RNA of 561 mer or 500 mer, the at least 90% homologous sequence encompasses mutant sequences that comprise 1 to 50 mismatched nucleotides (or 1 to 56 mismatched nucleotides in the case of the RNA of 561 mer) resulting from insertion, deletion or point mutation of nucleotides and that have the function of increasing the ability to produce a recombinant polypeptide such as an antibody in association with the expression of the mutant sequences themselves in host cells, or the function of suppressing the NfkBia expression. Hence, it is deemed that a sequence derived from NfkBia orthologue (xenogeneic homologous gene) which has some degree of sequence similarity (e.g., at least 70% homology) and is derived from a species different from a host cell also can be used as APES.

Alternatively, the sequence that can bind by base pairing encompasses a sequence that can bind to NfkBia mRNA under a condition such as an intracellular condition. Such a sequence encompasses, for example, a sequence that hybridizes under conditions known to the skilled person as highly stringent conditions and that has desired functions. One example of the highly stringent conditions is incubation of a polynucleotide and another polynucleotide in a hybridization buffer solution comprising 6×SSPE or SSC, 50% formamide, 5×Denhardt's reagent, 0.5% SDS and 100 µg/ml of a fragmented, denatured salmon sperm DNA, at a hybridization temperature of 42° C. for 12 to 16 hours (one of the polynucleotides may be adhered to the surface of such a solid as a membrane) and subsequent several washings of the resulting material with a wash buffer solution comprising 1×SSC and 0.5% SDS at an optimal temperature of 42° C. or higher. For other concrete conditions, refer to multiple experiment manuals that are well known to the skilled person, such as Sambrook et al., "Molecular Cloning: A Laboratory Manual (3rd Edition)", Cold Spring Harbor Laboratory Pr; and Ausubel et al., "Current Protocols in Molecular Biology", Maruzen Co., Ltd.

The novel nucleic acid molecule having APES activity or a nucleic acid molecule having the sequence complementary to the molecule is an important feature of the present invention.

In one embodiment, APES is a nucleic acid molecule having the function of suppressing the NfkBia expression or increasing the production of a recombinant polypeptide and is an RNA or DNA that can bind to the DNA or mRNA of the NfkBia gene derived from human, mouse, rat or hamster by base pairing. It is deemed that such a nucleic acid molecule comprises a sequence homologous or complementary to mRNA encoding NfkBia and can bind to the NfkBia gene or mRNA and inhibit its expression.

In one embodiment, APES is a small RNA of 19 to 25 nucleotides in length comprising the sequence complementary to a part of NfkBia mRNA, or a small RNA that has a sequence identical to the sequence except for one nucleotide and has the function of suppressing the NfkBia expression or increasing the production of recombinant polypeptides. The small RNA as referred to herein means a small non-coding RNA (snRNA), and snRNA encompasses miRNA.

In one embodiment, APES is an mRNA type non-coding RNA of at most 561 nucleotides in length or at most 500 nucleotides in length that comprises the sequence complementary to a part of NfkBia mRNA (for example, the sequence is a small non-coding RNA sequence as described above).

In one embodiment, APES is an mRNA type non-coding RNA of 561 to 1579 nucleotides in length or 500 to 1000 nucleotides in length that comprises the sequence complementary to a part of NfkBia mRNA (for example, the sequence is a small non-coding RNA sequence as described above).

One specific example of APES that was found in the transcript in CHO cells has a mouse AI462015-derived partial sequence or such a partial sequence in which one or several nucleotides have been substituted, deleted or added. In particular, included is a DNA sequence of 165 nucleotides that consists of the nucleotide sequence between G at nucleotide 4 and C at nucleotide 168 from the 5' end (SEQ ID NO: 2, APES165); the complementary (antisense) DNA sequence of the DNA sequence; a sequence comprising an RNA sequence transcribed from these DNA; or a partial sequence of any length in the sequence. Alternatively, included is a DNA sequence of 434 nucleotides that consists of the nucleotide sequence between G at nucleotide 4 from the 5' end and T at the 3' end (SEQ ID NO: 3, APES434); the complementary (antisense) DNA sequence of the DNA sequence; a sequence comprising an RNA sequence transcribed from these DNA; or a partial sequence of any length derived from the sequence. Also included is a nucleotide sequence comprising a sequence derived from a mammal such as human, hamster or rat that corresponds to the mouse AI462015 sequence; a partial sequence of the sequence comprising the mammal-derived sequence; or such a partial sequence in which one or several nucleotides have been substituted, deleted or added.

In one embodiment, APES has the nucleotide sequence between nucleotides 4 and 133 from the 5' end (SEQ ID NO: 4, APES130) in AI462015 or a partial sequence derived from the sequence. For example, included is the DNA sequence between nucleotides 4 and 68 from the 5' end (SEQ ID NO: 5, APES4-68) or the DNA sequence between nucleotides 69 and 133 from the 5' end (SEQ ID NO: 6, APES69-133) or the complementary DNA sequence thereof, or a sequence transcribed from these DNA.

In one embodiment, APES has the sequence of 52 nucleotides between nucleotides 40 and 91 from the 5' end (SEQ ID NO: 7) in AI462015 or a sequence derived from a partial sequence obtained by cleavage of the 52 nucleotides at any location. For example, included is the DNA sequence of the former part (the 29 nucleotides of APES40-68, the 24 nucleotides of APES40-63, or the 22 nucleotides of APES40-61) or the latter part (the 23 nucleotides of APES69-91) or the complementary DNA sequence thereof (corresponding to SEQ ID NOs: 8 to 11, respectively) or a sequence transcribed from these DNA.

The 52 nucleotides described above are a sequence identical to that of the complementary strand of the 3' untranslated region of the rat NfkBia gene except for one nucleotide. The 5' 24 nucleotides (APES40-63, SEQ ID NO: 9) are a sequence identical to that of the 3' untranslated region of the human NfkBia gene. The 5' 22 nucleotides (APES40-61, SEQ ID NO:10: AAGTACCAAAATAATTACCAAC) are a sequence identical to that of the complementary strand of the 3' untranslated region of NfkBia mRNA regardless of species such as rat, rhesus monkey, dog and horse. RNAi effect is expected to be produced by expressing in host cells a partial sequence complementary to the 3' untranslated region of the NfkBia gene. For example, it is possible that an RNA having a sequence complementary to 19 to 25 nucleotides of the above 52 nucleotides would act as a micro RNA (miRNA) on the untranslated region of NfkBia mRNA, thereby interfering with translational process.

Alternatively, APES has the sequence of 85 nucleotides between nucleotides 7 and 91 from the 5' end (SEQ ID NO: 29) in AI462015 or a sequence derived from a partial sequence obtained by cleavage of the 85 nucleotides at any location. It is possible that an RNA having a sequence complementary to 19 to 25 nucleotides of the above 85 nucleotides would act as a microRNA (miRNA) on the untranslated region of NfkBia mRNA, thereby interfering with translational process.

In one embodiment, APES has a sequence found in a search for siRNA of 21 nucleotides. Examples include miRNA sequences comprising the sequence complementary to the DNA sequence between nucleotides 84 and 104 (SEQ ID NO: 12, APES84-104) in AI462015, the DNA sequence between nucleotides 99 and 119 (SEQ ID NO: 13, APES99-119) or the DNA sequence between nucleotides 101 and 121 (SEQ ID NO: 14, APES101-121). The sequence between nucleotides 71 and 112 (SEQ ID NO: 16) in the above APES 69-133 is a region that has been quantified on GeneChip and actually expressed at a high level. Hence, it is deemed to be highly possible that APES84-104 would function as a miRNA.

Further, based on the structural or functional feature of APES, a new nucleic acid molecule having APES activity can be synthesized chemically or isolated from biological sources. The structural feature of APES is that it is a nucleic acid molecule comprising a sequence complementary to a part of target NfkBia mRNA. The nucleic acid molecule may be in any form, regardless of matters such as whether it is a DNA, DNA transcript, mRNA or cDNA, exosome RNA, chemically synthesized single-stranded RNA, or chemically synthesized double-stranded RNA. The functional feature is the increase of the ability to produce a recombinant polypeptide such as an antibody or the suppression of the NfkBia expression, in association with the expression of APES in host cells.

If APES is isolated from a biological source, it may be derived from any living organism without any particular limitation. Specific examples include APES derived from animals including primates such as human and chimpanzee; rodents such as mouse, rat and hamster; livestock such as cattle, pig and goat; birds such as chicken; fish such as zebrafish; insects such as fly; nematode; and the like. APES is preferably derived from human, a rodent, or the same species as a host cell. For example, when a strongly APES-expressing cell is a Chinese hamster ovary cell (CHO cell). APES is preferably derived from human, mouse or hamster.

Such a nucleic acid molecule can be prepared by a method known to the skilled person. For example, the nucleic acid molecule may be prepared in accordance with the following procedures: preparing total RNA from a cultured cell that has produced a recombinant polypeptide such as an antibody at a high level, synthesizing an oligonucleotide on the basis of a nucleic acid sequence of the present invention (e.g., APES165 of SEQ ID NO: 2), and carrying out PGR using the oligonucleotide as a primer to amplify cDNA having the features of APES. Further, after the preparation of a small RNA from the cultured cell that has produced a recombinant polypeptide such as an antibody at a high level, a cDNA library can be prepared to produce a small RNA comprising a partial sequence complementary to NfkBia mRNA on the basis of the nucleotide sequence of a cloned cDNA. The cDNA library also can be constructed by a method described in, for example, Sambrook, J. et al., Molecular Cloning, Cold Spring Harbor Laboratory Press (1989), after preparing a small RNA such as a microRNA (miRNA).

Furthermore, an APES-expressing genomic DNA can be isolated by determining the nucleotide sequence of the cDNA obtained and screening a genomic DNA library using the cDNA as a probe.

Specifically, the following procedures may be used: first, total RNA is isolated from cells, tissues, or the like that are likely to express APES of the present invention; for the isolation of mRNA, a known method such as the guanidine ultracentrifugation method (Chirgwin, J. M. et al., Biochemistry (1979) 18, 5294-5299) or the AGPC method (Chomczynski, P. and Sacchi, N., Anal. Biochem. (1987) 162, 156-159) is used to prepare total RNA, and then the total RNA is further purified using RNEASY® Mini Kit (QIAGEN) or the like.

From the total RNA obtained, cDNA is synthesized using a reverse transcriptase. cDNA also can be synthesized using SUPERSCRIPT™ II Reverse Transcriptase (Invitrogen) or the like. It is also possible to synthesize and amplify cDNA in accordance with the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) using 5-AMPLIFINDER™ RACE Kit (Clontech) and polymerase chain reaction (PCR) with a primer and the like.

A DNA fragment of interest is prepared from the resulting PCR product and ligated to a vector DNA to thereby prepare a recombinant vector. The vector is introduced into *E. coli* or the like, and then, colonies obtained are selected to prepare a desired recombinant vector. The nucleotide sequence of the DNA of interest can be confirmed by a known method such as the dideoxynucleotide chain termination method.

The DNA obtained can be modified using a commercially available kit or a known method. Such modification is, for example, the introduction of single nucleotide polymorphism using the site-directed mutagenesis method, or the like. The thus modified sequences are also included in the scope of the present invention as long as they have APES activity.

As used herein, the phrase "have (having) APES activity" refers to having the action of suppressing the NfkBia expression in a cultured host cell to thereby activate Nf-kappa B and thus increase the recombinant polypeptide-producing ability. The phrase refers univocally to having the function of suppressing the NfkBia expression by expression of the subject in a cell.

In some cases, a nucleic acid molecule having APES activity is referred to herein as the nucleic acid molecule of the present invention.

(2) Expression of APES

In the present invention, it was found that by using APES-expressing cells, preferably, strongly APES-expressing cells, the amount of polypeptides produced by the cells is increased.

A strongly APES-expressing cell means a cell into which APES has been artificially introduced using a vector or the like, and strong expression of APES means that the expression level of APES has been increased as compared with an original cell into which antibody gene has not yet been introduced. Examples of the original cell include, but are not particularly limited to, cells for use as hosts (e.g., CHO cells) in the production of recombinant proteins. If it is explained with reference to the Examples described later, a specific example is as follows: in a GENECHIP® experiment using an oligonucleotide array produced by AFFYMETRIX, Inc. (Affymetrix MOUSE430_2), signal values of AI462015 are 2000 or less in original cells into which antibody gene has not yet been introduced. An increase of the expression level of APES as compared with the values means that a signal value of AI462015 is, for example, twice or more as high as those values.

A strongly APES-expressing cell comprises endogenous or exogenous APES in the cell. Examples of the strongly APES-expressing cell include cells into which APES has been artificially introduced.

A cell into which APES has been artificially introduced can be prepared by a method known to the skilled person. For example, the cell can be prepared by incorporating an APES-encoding DNA sequence into a vector and transforming the vector into a cell.

The cell into which APES has been artificially introduced, as referred to herein, further encompasses cells in which endogenous APES has been activated by gene activation technology (refer to, for example, International Publication No. WO 94/12650 pamphlet) which resulted in strong expression of APES.

A typical example of the endogenous APES is APES as a DNA sequence encoded in the host cell genome. In the present invention, cells also can be used in which after introduction of antibody gene, the transcription of the endogenous APES has been activated because of some factor without using any gene activation technology, resulting in strong expression.

A vector into which an APES-encoding DNA sequence has been inserted also falls within the scope of the present invention. The vector of the present invention is useful for retaining the nucleic acid molecule of the present invention within or outside a host cell and expressing the nucleic acid molecule of the present invention. The vector of the present invention is also useful for permitting a host cell to express APES strongly. By permitting a host cell to express APES strongly, the amount of a desired polypeptide produced by the host cell can be increased.

For example, when *E. coli* is used as a host cell, it is preferred that the vector has an "ori" for amplification in *E. coli* (e.g., JM109, DH5α, HB101, XL1Blue) to achieve the amplification and preparation of a large quantity of the vector in *E. coli* or the like and also has a gene for selecting transformed *E. coli* (e.g., a drug resistance gene that allows discrimination using some drug (ampicillin, tetracycline, kanamycin, chloramphenicol)). Examples of the vector include M13 vectors, pUC vectors, pBR322, pBLUE-SCRIPT®, pCR-SCRIPT®, and the like. In addition to these vectors, pGEM-T, pDIRECT, pT7 and the like are enumerated if the vectors are used for subcloning and excision of cDNA.

(3) Expression Vector

In the present invention, when a vector is used for strong expression of APES and/or polypeptide production, an expression vector is especially useful. Examples of the expression vector that can be used in the present invention include mammal-derived expression vectors (e.g., pcDNA3 (Invitrogen), pEGF-BOS (Nucleic Acids. Res. 1990, 18(17), p5322), pEF, pCDM8), insect cell-derived expression vectors (e.g., "BAC-TO-BAC® baculovirus expression system" (GIBCO BRL), pBacPAK8), plant-derived expression vectors (e.g., pMH1, pMH2), animal virus-derived expression vectors (e.g., pHSV, pMV, pAdexLew), retrovirus-derived expression vectors (e.g., pZIpneo), yeast-derived expression vectors (e.g., "Pichia Expression Kit" (Invitrogen), pNV11, SP-Q01), Bacillus subtilis-derived expression vectors (e.g., pPL608, pKTH50), and the like.

The expression vector for expressing an exogenous polypeptide comprises a DNA encoding the polypeptide and an expression-regulating sequence capable of promoting the expression of the DNA. Likewise, the expression vector for expressing APES comprises a DNA encoding APES and an expression-regulating sequence capable of promoting the expression of the DNA. A single vector may be constructed to express both a polypeptide and APES. For example, if an APES or polypeptide gene that is a part of the host genome is activated using gene activation technology, an expression-regulating sequence that promotes the expression of such a host cell-derived DNA may be introduced.

Examples of the expression-regulating sequence include an appropriate promoter, enhancer, transcription terminator, a Kozak sequence containing a start codon (i.e., ATG) in a protein-encoding gene, a splicing signal for intron. a polyadenylation site, a stop codon, and the like. The vector can be appropriately constructed by the skilled person.

The expression-regulating sequence preferably contains a promoter/enhancer region capable of increasing the level of gene transcription in an animal cell to be used. The promoter/enhancer region involved in the expression of a gene encoding a desired polypeptide may contain a NF-κB-binding sequence.

When expression in mammalian cells such as CHO cells, COS cells and NIH3T3 cells is intended, the vector preferably has a promoter needed for expression in the cells, such as SV40 promoter (Mulligan et al., Nature (1979) 277, 108), MMLV-LTR promoter, EF1α promoter (Mizushima et al., Nucleic Acids Res. (1990) 18, 5322) or CMV promoter. More preferably, the vector also has a gene for selection of transformation into cells (e.g., a drug resistance gene that allows discrimination using a drag (e.g., neomycin, G418)). Examples of the vector having such characteristics include pMAM, pDR2, pBK-RSV, pBK-CMV, pOPRSV, pOP13 and the like.

Further, when the stable expression of a gene and the intracellular amplification of the copy number of the gene are intended, a method may be used in which, into CHO cells lacking a nucleic acid synthesis pathway, a vector having the DHFR gene which complements the lack (e.g., pCHOI) is introduced, followed by amplification with methotrexate (MTX). When transient expression of a gene is intended, a method may be used in which COS cells carrying a SV40 T antigen-expressing gene on the chromosome are transformed with a vector having the replication origin of SV40 (e.g., pcD). As the replication origin, a replication origin derived from polyomavirus, adenovirus, bovine papillomavirus (BPV) or the like also can be used. Further, to amplify the gene copy number in a host cell system, the expression vector can contain a selection marker such as the aminoglycoside transferase (APH) gene, thymidine kinase (TK) gene, E. coli xanthine-guanine phosphoribosyl transferase (Ecogpt) gene, or dihydrofolate reductase (dhfr) gene.

(4) Host Cell

The cell to be used in the present invention may be either a natural cell capable of producing a desired polypeptide or a cell into which a DNA encoding a desired polypeptide has been introduced. Preferably, a transformed cell into which a DNA encoding a desired polypeptide has been introduced is used.

One example of the transformed cell into which a DNA encoding a desired polypeptide has been introduced is a host cell that has been transfected with an expression vector containing at least a DNA encoding a desired polypeptide and that has expressed endogenous or exogenous APES strongly.

Further, in the present invention, the cell into which "a DNA (or a gene) has been introduced" encompasses cells transfected with exogenous DNA as well as cells in which endogenous DNA has been activated using gene activation technology (refer to, for example, International Publication No. WO 94/12650 pamphlet) which resulted in the expression of a protein corresponding to the DNA or the initiation or increase of the DNA transcription.

When a cell into which APES has been artificially introduced is used to produce a desired polypeptide, the sequence of the introduction of APES and a gene encoding the desired polypeptide is not particularly limited; APES may be introduced before the introduction of the gene encoding the desired polypeptide, or the gene encoding the desired polypeptide may be introduced before the introduction of APES. Alternatively, APES and the gene encoding the desired polypeptide may be introduced simultaneously.

When a vector is used, APES and the gene encoding the desired polypeptide may be introduced simultaneously using a single vector, or they may be introduced separately using a plurality of vectors.

The cell to be used in the present invention is not particularly limited. It may be any cell such as a eukaryotic cell (e.g., animal cell, plant cell, yeast) or a prokaryotic cell (e.g., E. coli and B. subtilis). Animal cells derived from insects, fish, amphibia, reptiles and mammals are preferred, and mammalian cells are particularly preferred. The origins of the mammalian cells are primates such as human and chimpanzee, rodents such as mouse, rat and hamster, and the like, preferably human and rodents. Further, it is preferred that the cell of the present invention is cultured mammalian cells that are usually often used for the expression of polypeptides, such as CHO cells, COS cells, 3T3 cells, myeloma cells, BHK cells, HeLa cells and Vero cells. For the expression of a large quantity of a desired polypeptide, CHO cells are particularly preferably used. In particular, dhfr-CHO (Proc. Natl. Acad. Sci. USA (1980) 77, 4216-4220), which is CHO cells lacking the DHFR gene, or CHO K-1 (Proc. Natl. Acad. Sci. USA (1968) 60, 1275) can be advantageously used as CHO cells.

In particular, DG44 strain, DXB-11 strain, K-1 or CHO-S is preferred as the above CHO cell, and DG44 or DXB-11 strain is particularly preferred.

The host cell of the present invention can be used, for example, as a production system for the production or expression of a desired polypeptide. If a DNA encoding a desired polypeptide is introduced into a strongly APES-expressing host cell, the desired polypeptide can be produced at a high level. Into the host cell of the present invention, a DNA encoding either a taurine transporter (TauT) or an anion exchanger (AE1) (the DNA may be incorporated into a vector) may be further introduced. Into the host cell of the present invention, a DNA encoding either cysteine sulfinic acid decarboxylase (CSAD) or alanine transferase (ALT1) may be still further introduced. For details, refer to WO 2007/119774, WO 2008/114673, WO 2009/020144 and WO 2009/054433.

Exogenous DNA (which may be incorporated into a vector) can be introduced into the host cell by a method such as the calcium phosphate method, the DEAE dextran method, a method using cationic ribosome DOTAP (Boehringer Mannheim), electroporation, the Nucleofection method (amaxa), or lipofection.

(5) Intended Polypeptide

The polypeptide to be produced by the method of the present invention is not particularly limited. It may be any polypeptide such as an antibody (e.g., anti-IL-6 receptor antibody, anti-IL-6 antibody, anti-glypican-3 antibody, anti-CD3 antibody, anti-CD20 antibody, anti-GPIIb/IIIa antibody, anti-TNF antibody, anti-CD25 antibody, anti-EGFR antibody, anti-Her2/neu antibody, anti-RSV antibody, anti-CD33 antibody, anti-CD52 antibody, anti-IgE antibody, anti-CD11a antibody, anti-VEGF antibody, anti-VLA4 antibody) or a physiologically active protein (e.g., granulocyte colony-stimulating factor (G-CSF), granulocyte-macrophage colony-stimulating factor (GM-CSF), erythropoietin, interferon, interleukin (e.g., IL-1, IL-6), t-PA, urokinase, serum albumin, blood coagulation factor, PTH). An antibody is particularly preferred, and may be any antibody such as a natural antibody, a low molecular antibody (e.g., Fab, scFv, sc(Fv)2), a chimeric antibody, or a humanized antibody.

(6) Production of Polypeptide

A polypeptide of interest can be obtained by culturing the host cell described above, producing a desired polypeptide and collecting the polypeptide.

For culturing the cell, media that are used in common cell (preferably, animal cell) cultures can be used. These media generally contain amino acids, vitamins, lipid factors, energy sources, osmotic regulators, iron sources and pH buffers. It is generally appropriate that the contents of these components fall within the following ranges: amino acids 0.05-1500 mg/L, vitamins 0.001-10 mg/L, lipid factors 0-200 mg/L, energy sources 1-20 g/L, osmotic regulators 0.1-10000 mg/L, iron sources 0.1-500 mg/L, pH buffers 1-10000 mg/L, trace metal elements 0.00001-200 mg/L, surfactants 0-5000 mg/L, growth cofactors 0.05-10000 µg/L and nucleosides 0.001-50 mg/L. However, the contents are not limited to these ranges and can be appropriately determined depending on the type of the cell to be cultured, the type of the desired polypeptide, and the like.

In addition to the components described above, for example, trace metal elements, surfactants, growth cofactors, nucleosides and the like may be added.

Specific examples include amino acids such as L-alanine, L-arginine, L-asparagine, L-aspartic acid, L-cysteine, L-cystine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine and L-valine (preferably, L-alanine, L-arginine, L-asparagine, L-aspartic acid, L-cystine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine); vitamins such as i-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin B12 and ascorbic acid (preferably, biotin, folic acid, lipoic acid, nicotinamide, calcium pantothenate, pyridoxal hydrochloride, riboflavin, thiamine hydrochloride, vitamin B12 and ascorbic acid); lipid factors such as choline chloride, choline tartrate, linoleic acid, oleic acid and cholesterol (preferably, choline chloride); energy sources such as glucose, galactose, mannose and fructose (preferably, glucose); osmotic regulators such as sodium chloride, potassium chloride and potassium nitrate (preferably, sodium chloride); iron sources such as iron EDTA, ferric citrate, ferrous chloride, ferric chloride, ferrous sulfate, ferric sulfate and ferric nitrate (preferably, ferric chloride, iron EDTA and ferric citrate); and pH buffers such as sodium hydrogencarbonate, calcium chloride, sodium dihydrogen phosphate, HEPES and MOPS (preferably, sodium hydrogencarbonate). Media containing any one(s) of these components can be given as examples.

In addition to the above components, for example, the following components may be added: trace metal elements such as copper sulfate, manganese sulfate, zinc sulfate, magnesium sulfate, nickel chloride, tin chloride, magnesium chloride and sodium subsilicate (preferably, copper sulfate, zinc sulfate and magnesium sulfate); surfactants such as TWEEN 80® and Pluronic F68; growth cofactors such as recombinant insulin, recombinant IGF-1, recombinant EGF, recombinant FGF, recombinant PDGF, recombinant TGF-α, ethanolamine hydrochloride, sodium selenite, retinoic acid and putrescine hydrochloride (preferably, sodium selenite, ethanolamine hydrochloride, recombinant IGF-1 and putrescine hydrochloride); nucleosides such as deoxyadenosine, deoxycytidine, deoxyguanosine, adenosine, cytidine, guanosine and uridine; and the like. It is to be noted that in preferred examples of above media, an antibiotic such as streptomycin, penicillin G potassium or gentamicin or a pH indicator such as Phenol Red may be contained.

The pH of the medium varies depending on the cell to be cultured. pH6.8-7.6 is generally appropriate, and pH7.0-7.4 is appropriate in many cases.

It is also possible to use a commercially available medium for animal cell culture, such as D-MEM (Dulbecco's Modified Eagle Medium), D-MEM/F-12 1:1 Mixture (Dulbecco's Modified Eagle Medium: Nutrient Mixture F-12), RPMI1640, CHO-S-SFM II (Invitrogen), CHO-SF (Sigma-Aldrich), EX-CELL 301 (JRH Biosciences), CD-CHO (Invitrogen), IS CHO-V (Irvine Scientific) or PF-ACF-CHO (Sigma-Aldrich).

The medium may be a serum-free medium.

When the host cell is CHO cells, a method known to the skilled person can be used to culture the CHO cells. For example, CHO cells can be usually cultured in a gas-phase atmosphere at a $CO_2$ concentration of 0 to 40%, preferably 2 to 10%, at 30 to 39° C., preferably about 37° C.

An appropriate culture period for producing a desired polypeptide is usually 1 day to 3 months, preferably 1 day to 2 months, more preferably 1 day to 1 month.

As various culture devices for animal cell culture, the following devices can be used for culture: for example, fermenter type tank culture devices, air lift type culture devices, culture flask type culture devices, spinner flask type culture devices, microcarrier type culture devices, fluidized bed type culture devices, hollow fiber type culture devices, roller bottle type culture devices and packed bed type culture devices.

Culture may be performed by any method such as batch culture, fed-batch culture or continuous culture. Among them, fed-batch culture or continuous culture is preferred, and fed-batch culture is more preferred.

The polypeptide obtained can be isolated from the inside of a host cell or from its outside (e.g., media) and purified into a substantially pure and homogenous polypeptide. The isolation and purification of the polypeptide may be performed using a common isolation and purification method in polypeptide purification, and are not limited in any way. For example, polypeptides can be isolated and purified by appropriately selecting and combining chlomatography columns, filters, ultrafiltration, salting-out, solvent precipitation, solvent extraction, distillation, immunoprecipitation, SDS-polyacrylamide gel electrophoresis, isoelectric focusing, dialysis, recrystallization, and the like.

Examples of the chromatography include affinity chromatography, ion-exchange chromatography, hydrophobic chromatography, gel filtration, reverse-phase chromatography, adsorption chromatography, and the like (Strategies for Protein Purification and Characterization: A Laboratory Course Manual. Ed. Daniel R. Marshak et al., Cold Spring Harbor Laboratory Press, 1996). These chromatographies can be carried out using liquid-phase chromatography such as HPLC or FPLC. The present invention also encompasses polypeptides highly purified by these purification methods.

It is to be noted that before or after the purification of polypeptides, it is also possible to give optional modifications or remove a partial peptide by allowing an appropriate polypeptide modification enzyme to act on the polypeptides. Examples of the polypeptide modification enzyme include trypsin, chymotrypsin, lysyl endopeptidase, protein kinase, glucosidase, and the like.

(7) Pharmaceuticals

When the polypeptide produced by the method of the present invention has a biological activity that can be utilized as a medicament, the polypeptide can be mixed with a pharmaceutically acceptable carrier or additive and formulated to produce a pharmaceutical.

Examples of the pharmaceutically acceptable carrier or additive include water, pharmaceutically acceptable organic solvents, collagen, polyvinyl alcohol, polyvinylpyrrolidone, carboxyvinyl polymers, sodium carboxymethyl cellulose, sodium polyacrylate, sodium alginate, water-soluble dextran, sodium carboxymethyl starch, pectin, methyl cellulose, ethyl cellulose, xanthane gum, gum arabic, casein, agar, polyethylene glycol, diglycerin, glycerin, propylene glycol, Vaseline, paraffin, stearyl alcohol, stearic acid, human serum albumin (HSA), mannitol, sorbitol, lactose, surfactants acceptable as pharmaceutical additives, and the like.

The actual additive is selected from the foregoing additives, either alone or in an appropriate combination, according to the dosage form of the therapeutic agent of the present invention, but the actual additive is definitely not limited thereto. For example, in case of using as a formulation for injection, a material can be used that is obtained by dissolving the purified polypeptide in a solvent such as physiological saline, a buffer solution or a glucose solution and then adding to the resulting solution an adsorption inhibitor such as TWEEN 80®, TWEEN 20®, gelatin or human serum albumin. Alternatively, a freeze-dried material may be used to prepare a dosage form that is dissolved and reconstituted prior to use, and an excipient that can be used for the freeze-drying is, for example, a sugar alcohol or sugar, such as mannitol or glucose.

The effective amount of administration of the polypeptide is appropriately selected according to the type of the polypeptide, the type of diseases to be treated or prevented, the age of patients, the seriousness of the diseases, and the like.

For example, when the polypeptide is an anti-glypican antibody, the effective amount of administration is selected from the range of 0.001 mg to 1000 mg per kg of body weight per administration. Alternatively, an amount of administration of 0.01 to 100000 mg/body can be selected per patient. However, the effective amount is not limited to these ranges.

The polypeptide can be administered either orally or parenterally, but parenteral administration is preferred. Specific examples include injection (e.g., systemic or local administration by intravenous injection, intramuscular injection, intraperitoneal injection, subcutaneous injection or the like), transnasal administration, transpulmonary administration, percutaneous administration and the like.

(8) Suppression of NfkBia Expression

According to the present invention, in the method of producing a desired polypeptide by culturing an animal cell into which a DNA encoding the polypeptide has been introduced, the production amount of the desired polypeptide can be increased by decreasing the expression level of nuclear factor kB inhibitor a (NfkBia) in the host cell. The NfkBia gene is an essential gene, and the complete suppression of the gene leads to cell death. Hence, it is conceivable that suppressing the expression of the NfkBia gene moderately is important in the method of the present invention.

For these reasons, the scope of the present invention includes the method of producing a desired polypeptide by culturing an animal cell into which a DNA encoding the polypeptide has been introduced, comprising the step of decreasing the expression level of NfkBia in the cell to a level lower than that in a parent cell into which antibody gene has not yet been introduced.

As a method of decreasing the NfkBia expression, the expression can be inhibited by the inhibition of transcription from the NfkBia gene, the degradation of mRNA, the inhibition of translation from mRNA, or the inhibition of the function (binding) of translation product. As compared with cases in which this method of decreasing the NfkBia expression is not used, the expression level of NfkBia is controlled to 70% or lower, preferably 60% or lower, more preferably 50% or lower, resulting in the increase of the production amount of the desired polypeptide. In other words, the expression level of the NfkBia gene necessary to avoid cell death is, for example, 20% or higher, preferably 30% or higher.

A specific means for inhibiting the NfkBia expression is deemed to be the use of an antisense oligonucleotide, a ribozyme or a nucleic acid molecule that causes RNA interference (RNAi), such as dsRNA, siRNA, shRNA or miRNA. mRNA type non-coding RNAs which are called "large intergenic (or intervening) long noncoding RNAs (lincRNAs)", other mRNA type non-coding RNAs, decoy oligos or aptamers also can be used. These nucleic acid molecules each comprise a sequence homologous or complementary to mRNA encoding NfkBia and can bind to the NfkBia gene or mRNA and inhibit its expression. APES (or PPES) is such a nucleic acid molecule.

The nucleic acid molecule that can be used to inhibit the NfkBia expression is, for example, a small RNA of 19 to 25 nucleotides in length comprising the sequence complementary to a part of NfkBia mRNA, or a small RNA that has a sequence identical to the sequence except for one nucleotide and has the function of inhibiting the NfkBia expression.

By expressing in a host cell such a small RNA that inhibits the NfkBia expression, the expression level of nuclear factor κB inhibitor α (NfkBia) can be decreased. A typical method for expressing in a host cell the small RNA that inhibits the NfkBia expression can be the introduction of a vector comprising a DNA encoding such a small RNA into the cell.

It is also possible to inhibit the NfkBia expression by introducing into the cell a dsRNA formed by binding of a sense RNA and antisense RNA against NfkBia mRNA or a partial sequence thereof to each other.

Before measuring the NfkBia expression level, the sequence of NfkBia mRNA that has been expressed in a target cell and can be quantified by a TAQMAN® method has to be determined. For example, the NfkBia partial sequences (SEQ ID NOs: 19 and 28) and TAQMAN® probe set (SEQ ID NOs: 20-22) that were used in this study can be shown by FIG. 12. These TAQMAN® probes can be designed using Primer Express® Software (Applied Biosystems) or the like. The above NfkBia partial sequence (SEQ ID NO: 28) was also confirmed as an NF-kappa-B inhibitor alpha-like sequence in CHO K1 cells and matched our sequence in PCR cloning. In the sequence, the expression of the region between 64 nucleotides upstream and 132 nucleotides upstream of the stop codon TGA (907-909) can be quantified.

A typical measurement instrument is, for example, 7900HT Sequence Detection System produced by Applied Biosystems (ABI), and all kits and reagents can be purchased. Hence, the quantification can be performed in accordance with a protocol recommended by ABI.

EXAMPLES

The present invention is concretely described below with reference to the Examples shown below. It should be noted that these Examples are provided for illustrating the present invention, not for limiting the scope of the present invention.

Example 1

GENECHIP® Experiment for Analyzing Various Gene-Introduced CHO Cells

A GENECHIP® experiment was conducted in accordance with a common procedure using an oligonucleotide array produced by AFFYMETRIX, Inc. (Affymetrix MOUSE430_2), provided that since any hamster array had not been commercialized, Mouse Genome 430 2.0 Array was used. Optimization of hybridization conditions resulted in the detection of present calls in 8 of 16 mouse gene probes on Test 3 Array, and it became possible to quantify the expression of transcript in hamsters when the nucleotide sequence homology to mouse sequences was about 90% or higher.

From cells exhibiting the strong expression of various genes, high-purity total RNA was prepared, and then, cDNA was synthesized using the total RNA and an oligo dT primer containing a T7 promoter sequence (T7-(T)24). Next, a biotin-labeled cRNA was synthesized from the cDNA through a transcription reaction using Bio-11 CTP, Bio-16 UTP and MEGASCRIPT® T7 Kit (Ambion). After the cRNA was subjected to column purification, the resulting high-quality cRNA whose molecular weight was confirmed on electrophoresis to correspond to 18s to 28s rRNA was fragmented to prepare GENECHIP® samples of a uniform size. To the GENECHIP® samples prior to use, a hybridization sample solution was added, followed by cryopreservation at −80° C. The sample solution was heat-treated immediately before use, centrifuged and applied to Mouse Genome 430 2.0 Array. Incubation was performed at 45° C. for 16 hours in an oven specialized for hybridization, while rotating the arrays. The samples were recovered, and the arrays were washed repeatedly, dyed with streptavidin R-phycoerythrin and then scanned.

The GENECHIP® signal values of the transcripts on the arrays (about 45,000) were compared, and as a result, an mRNA type non-coding RNA UG_GENE=AI462015 (Affymetrix MOUSE430_2, 1420088_AT) was identified as a transcript the expression of which was high intensity and markedly increased on mouse genome in a subcultured DG44 cell that produced at least 900 mg/L of MAb1 (anti-IL-6R antibody; tocilizumab, Product name: ACTEMRA®) on the 10th day of a 1L-jar fed-batch culture and that strongly expressed MAb1 (anti-IL-6R antibody), TAUT and CSAD (FIG. 1: the sequence of the AI462015 transcript).

AI462015 is an mRNA type non-coding RNA of 437 nucleotides and its sequence exists on the complementary strand near the 3' untranslated region (56590831-56590397) of NfkBia mRNA in mouse genome 12. There were possibilities that the AI462015 transcript would act directly on the untranslated region of NfkBia mRNA and inhibit translation or that a part of the sequence of 437 nucleotides would function as a small RNA and degrade NfkBia mRNA.

For example, the sequence of 52 nucleotides that is the sequence between A at nucleotide 40 and A at nucleotide 91 from the 5' end (AAGTACCAAAATAATTAC-CAACAAAATACAACATATACAACATTTACAAGAA: SEQ ID NO: 7) in the AI462015 sequence matched the complementary strand of the 3' untranslated region of rat NfkBia mRNA (1478-1529, GENE ID: 25493 NfkBia) except for one nucleotide (A at nucleotide 61 from the 5' end in AI462015). Further, the sequence of 24 nucleotides comprising the sequence between A al nucleotide 40 and A at nucleotide 63 (AAGTACCAAAATAATTACCAACAA: SEQ ID NO: 9) in AI462015 is the complementary strand of the partial sequence of the 3' untranslated region of human NfkBia mRNA (TTGTTGGTAATTATTTTGGTACTT, 1490-1513: SEQ ID NO: 24). In light of these points, it was predicted that 19 to 25 nucleotides that are a part of the 52 nucleotides would act on the NfkBia mRNA of CHO cells, serving as a microRNA, or that partial sequences would act on the NfkBia mRNA of CHO cells, serving as antisense RNAs.

Figure 23:
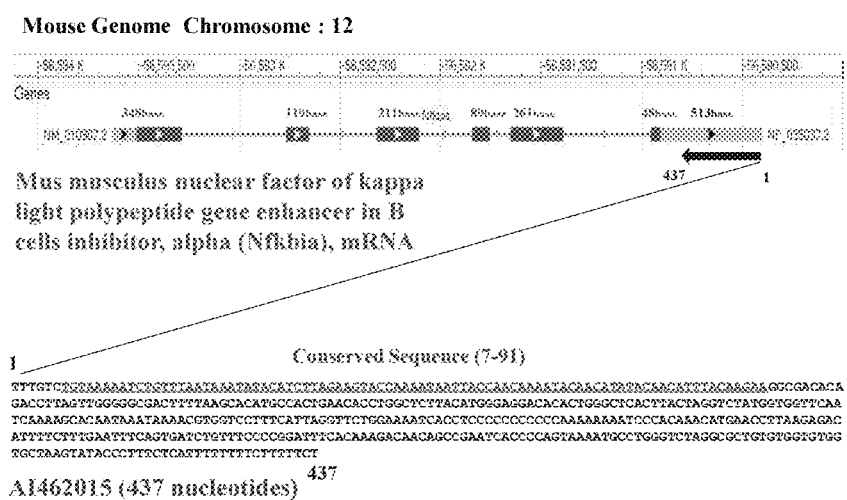
FIG. 23 shows that AI462015 is the complementary strand of mouse Nfkbia mRNA (Example 8) (SEQ ID NO: 39).

Further, according to updated information (Example 8), for example, the sequence of 85 nucleotides that is the sequence between T at nucleotide 7 and A at nucleotide 91 from the 5' end (the underlined part shown in FIGS. 23 and 24; SEQ ID NO: 29) (TGTAAAAATCTGTTTAATAAATATACATCTTAGAAG TACCAAAATAATTACCAACAAAATACAACATATACA ACATTTACAAGAA) in the AI462015 sequence matched the complementary strand of the 3' untranslated region of rat NfkBia mRNA (1478-1562, GENE ID: 25493 NfkBia, SEQ ID NO: 31) except for one nucleotide (A at nucleotide 70 from the 5' end in AI462015) (Matching=84/85, FIG. 25b). Likewise, the sequence was confirmed to be homologous to the sequences of human (Matching=75/85, FIG. 25a, SEQ ID NO: 30), chimpanzee (Matching=75/85, FIG. 25c, SEQ ID NO: 32), rhesus monkey (Matching=74/85, FIG. 25d, SEQ ID NO: 33), and cattle (Matching=76/85, FIG. 25e, SEQ ID NO: 34). Hence, it is deemed that 19 to 25 nucleotides that are a part of the 85 nucleotides (Conserved Sequence 7-91) act on animal cells or mammalian cells regardless of species, serving as a microRNA, or that partial sequences act on animal cells or mammalian cells regardless of species, serving as antisense RNAs. Thus, it was predicted that they also would act on the NfkBia mRNA of cultured animal cells, preferably mammalian cells such as CHO cells.

Example 2

Identification of Transcript Expressed at an Increased Level in Highly Antibody-Producing Cells In Example 1, the expression level of the transcript AI462015 was increased in the DG44 cell producing MAb1 (anti-IL-6R antibody; tocilizumab, Product name: ACTEMRA®) at a high level (FIG. 2). Likewise, when a different antibody (MAb2: anti-glypican 3 antibody; GC33 (refer to WO 2006/006693)) was produced at a high level in a different host cell (CHO-DXB11s), the increased expression of the AI462015 transcript was observed (FIG. 3).

As shown in FIG. 2, when the taurine transporter (TauT) gene was strongly expressed, the cysteine sulfinic acid decarboxylase (CSAD) gene was strongly expressed (data not shown), and TauT and CSAD were strongly co-expressed, in a CHO-DG44 cell in each case, the expression levels of the transcript AI462015 were all comparable. In contrast, in a cell in which TauT and CSAD were strongly co-expressed and additionally Mab (anti-IL-6 receptor antibody) was strongly expressed, aberrant increase of AI462015 (7 times higher than the host cell) was observed, and the expression level was also shown by an aberrantly high GENECHIP® signal value (10,000 or higher). Considering that the expression intensities of GAPDH as a control were comparable among cells, the increased expression of the transcript AI462015 was found to be specific in the cell producing Mab1 antibody at a high level. The same applies to the case shown in FIG. 3; when the MAb2 (anti-glypican 3 antibody) gene was strongly expressed in a CHO-DXB11s cell, the increased expression of the AI462015 sequence (13 times higher than the average value among cells each strongly expressing TauT, CSAD or AE1) was found to be specific in the cell producing MAb2 antibody at a high level.

The above results show that highly antibody-producing cells that grew stably on the 3rd day of shaker subculture expressed the AI462015 sequence at aberrantly high levels.

Under production culture conditions on the 3rd day of a 1L-jar culture, the aberrantly increased expression of the AI462015 sequence was also observed. As shown in FIG. 4, two types of highly antibody-producing cells producing about 1200 to 1400 mg/L of MAb1 (anti-IL-6R antibody) on the 10th day of a 1L-jar fed-batch culture exhibited high GeneChip signal values of 5,000 or higher. Because of the differences in culture conditions, the GeneChip signal values measured on the 3rd day of the 1L-jar fed-batch culture were about 50% of the value in the shaker culture. However, on the 13th day at the late stage of the 1L-jar fed-batch culture, it was found that the expression intensity of the AI462015 sequence had been increased to a level comparable to that in the shaker subculture, showing aberrantly high signal values (FIG. 5). On the other hand, a low antibody-producing and strongly MAb1-expressing DXB11s cell (300 mg/L or less on the 7th day of hydrolysate-free shaker culture; 500 mg/L or less even in hydrolysate-added culture) did not exhibit increased expression of the AI462015 sequence on the 3rd day of a 1L-jar culture even under conditions in which a hydrolysate that contributes to higher production (Hy-Fish or Procine Lysate) was added (FIG. 6).

The experimental results show the high amount of antibody produced in the strongly MAb1-, TauT- and CSAD-expressing DG44 cell that showed a high signal value in FIG. 2 (the amount was 640 mg/L on the 7th day of hydrolysate-free shaker culture), the high amount of antibody produced in the strongly MAb2-expressing DXB11s cell that showed a high signal value in FIG. 3 (the amount was 640 mg/L on the 7th day of hydrolysate-free shaker culture), and no increase of the signal value observed even when a hydrolysate that contributes to higher antibody production was added as shown in FIG. 6. In light of these experimental results, it was deemed that "a cell expressing a high level of the AI462015 sequence has high antibody-producing potential".

Example 3

Example of Higher Production Resulting from Strong Expression of APES in Antibody-Producing Cells To demonstrate that the expression level of the AI462015 sequence correlates with the level of antibody-producing potential, plasmids expressing a part of the AI462015 sequence were each introduced into the DXB11s cell that exhibited low antibody-producing potential and strong expression of MAb1 in FIG. 6, and then, strong expression was induced and the antibody-producing potentials were compared.

Of the sequence of the mouse genome-derived transcript AI462015 (FIG. 1; 437 nucleotides), partial sequences (containing an AI462015 probe sequence of Affymetrix GeneChip): the sequence between G at nucleotide 4 from the 5' end and T at the 3' end was named as APES434 and the sequence between G at nucleotide 4 and C at nucleotide 168 from the 5' end was named as APES165. Two types of expression units were thus prepared (APES is short for Antibody Production Enhancing Sequence). Kozak sequence-added expression units were synthesized to construct pHyg-APES434 (FIG. 7) and pHyg-APES165 (FIG. 8) each of which was expressed at high levels under a CMV promoter, and pHyg-null (FIG. 9).

NUCLEOFECTOR™ which is a system for gene introduction produced by Amaxa (currently, LONZA), was used to introduce the expression plasmids into the strongly MAb1-expressing DXB11s cells, which were low antibody-producing strains in FIG. 6. After selecting all cell strains that highly grew on a 96-well plate in the presence of a selection medium containing hygromycin (200 μg/ml), they were expanded to 24-well plate, and the amounts of antibody production were compared. The numbers of the selected strains are as follows: pHyg-APES434 (N=38), pHyg-APES165 (N=60) and pHyg-null (N=11), and it was expected from these strain numbers that a positive effect would be produced by the introduction of the strongly APES-expressing plasmids. Since no cell growth was observed on the 13th day of a static culture in the 24-well plate containing a 1 mL subculture medium, the amounts of antibody production and the cell numbers were measured. The average values of the amounts of antibody production were pHyg-APES434 (44.3 mg/L), pHyg-APES165 (41.2 mg/L) and pHyg-null (21.9 mg/L), and the cell numbers (average values) were pHyg-APES434 ($9.27 \times 10^5$ cells/mL), pHyg-APES165 ($11.39 \times 10^5$ cells/mL) and pHyg-null ($7.76 \times 10^5$ cells/mL). The pHyg-APES434-introduced cell and the pHyg-APES165-introduced cell were both statistically superior to the pHyg-null as a control (t-test, P<0.001, FIG. 10).

The above results show that the strong expression of the nucleic acid sequence comprising the 5' 165 bp of the AI462015 transcript (e.g., APES165, which is the DNA transcript of SEQ ID NO: 2, or APES434, which is the DNA transcript of SEQ ID NO: 3) increased the antibody-producing potential of the cells.

Example 4

Suppression of NfkBia Expression in Highly Antibody-Producing CHO Cells

As described in Example 1, the AI462015 sequence exists on the complementary strand near the 3' untranslated region (the 3' 78 bp) of the NfkBia gene in mouse genome 12; the 22 nucleotides (AAGTACCAAAATAATTACCAAC; SEQ ID NO: 10) contained in the AI462015 sequence are a sequence identical to that of the complementary strand of the 3' untranslated region (1492-1513) of the human NfkBia gene and are conserved regardless of species such as rat, rhesus monkey, dog and horse, and hence, there is a possibility that the 22 nucleotides would cause RNA interference and degrade NfkBia mRNA, serving as a microRNA; or the 21 nucleotides (CATATACAACATTTACAAGAA; SEQ ID NO: 15) from C at nucleotide 71 from the 5' end, which correspond to the former part of the specific probe sequence region (42 bp) (CATATACAACATTTACAAGAAGGCGACACAGACC TTAGTTGG; SEQ ID NO: 16) on an AFFYMETRIX oligonucleotide array (Affymetrix MOUSE430_2) that is capable of quantifying the AI462015 expression, are the sequence complementary to the sequence between nucleotides 1478 and 1498 of rat NfkBia mRNA. In light of the foregoing, there was a possibility that the AI462015 sequence-derived nucleic acid molecule would interfere with NfkBia mRNA (RNA interference), suppress its expression and thereby maintain the homeostasis of highly antibody-producing CHO cells (Lethality of knockout mice: postnatal) (Note: It was found later that the AI462015 transcript correspond to the complementary strand of 513 nucleotides in the 3' untranslated region of the mouse NfkBia gene. Refer to Example 8. Further, it was confirmed that the sequence between nucleotides 71 and 112 (SEQ ID NO: 16) of AI462015 that was quantified with mouse GENECHIP® was a transcript in CHO cells.)

In relation to these matters, the present inventors tried a procedure to quantify the expression level of NfkBia mRNA in the highly AI462015-expressing cells that had high antibody-producing potential, to confirm the suppression of the NfkBia mRNA expression.

Since the sequence of NfkBia mRNA in CHO cells was unknown, probes (5' ACTTGGTGACTTTGGGTGCT and 5' GCCTCCAAACACACAGTCAT) (SEQ ID NOs: 17 and 18, respectively) were designed using sequences conserved in the amino acid coding regions of mouse and rat (for the both regions, 942 nucleotides: 314 amino acids) to produce 325 bp PCR products. It is deemed that the 325 bp subjected to PCR cloning is a partial sequence of CHO cell-derived NfkBia mRNA, in light of the sequence homology (FIG. 11).

The expression of NfkBia mRNA could not be quantified with Mouse Genome 430 2.0 Array (Example 1), possibly because the probe sequence corresponds to a species-specific sequence of CHO cells. Meanwhile, the comparison of the 325 bp PCR products showed that the NfkBia mRNA expression was suppressed in the highly antibody-producing cells that exhibited increased expression of the AI462015 sequence (Lanes 3 and 4) as compared with strongly gene-expressing cells that had not produced antibody (Lanes 1 and 2). Further, a TaqMan probe set capable of quantifying a partial sequence of the 325 bp was designed (FIG. 12) and quantification was performed by RT-PCR. As a result, it was found that the NfkBia mRNA expression in the highly antibody-producing cells was suppressed to about 50% of the level in the cells that had not produced antibody (FIG. 13).

In light of these findings, it is deemed that the NfkBia mRNA expression was suppressed in the highly antibody-producing cells and consequently the antibody-producing potential was increased. In the promoter/enhancer regions of the expression plasmids used by the present inventors for the expression of antibody genes, at least a plurality of NfkB-binding sites actually exist (FIG. 14; the NfkB-binding sites on the mouse CMV IE2 promoter). These enhancer regions are essential for high expression of antibody genes. Thus, it is deemed that one factor of the high antibody production is that NfkB activated by the suppression of the NfkBia expression is translocated into the nucleus, followed by the enhancement of the promoter activity.

Example 5

Analysis of MicroRNA Increased in Highly Antibody-Producing CHO Cells

As illustrated by FIG. 15, Mir-X™ miRNA First-Strand Synthesis Kit (Clontech) was used to analyze microRNA. The 3' ends of the small RNAs prepared from the following cells were poly(A)-tailed: a highly MAb1 (anti-IL-6R antibody)-producing DXB11s cell and highly MAb1 (anti-IL-6R antibody)-producing and strongly TAUT-expressing DXB11s cell, both of which had been in subculture, and a DXB11s host cell into which antibody gene had not yet been introduced. After that, an adapter having an oligo dT at the 3' ends and a PCR primer sequence (mRQ 3' primer) at the 5' ends was subjected to priming to synthesize first-strand cDNAs. qPCR was carried out using the resulting cDNAs as templates, the mRQ 3' primer and an expected APES sequence-derived microRNA-specific primer (APES 40-61 5' primer or APES 71-91 5" primer), and further, U6 snRNA 5' primer as a positive control (30 cycles of 95° C. for 5 sec, 60° C. for 20 sec). The PCR reaction liquids obtained were purified and then electrophoresed on 3% agarose gel. As illustrated by FIG. 16, bands of intended size were detected by the PCR using the APES 40-61 5' primer and the U6 snRNA 5' primer. As shown by Lanes 1, 2 and 3, the 22 nucleotides of APES 40-61 (AAGTACCAAAATAATTAC-CAAC; SEQ ID NO: 10) were expressed at high levels in the highly MAb1 (anti-IL-6R antibody)-producing cells. The expression level of the U6 snRNA (Lane 4) as a positive control was comparable in any cells, and the presence of APES 71-91 (CATATACAACATTTACAAGAA; SEQ ID NO: 15) was not confirmed (data not shown). Based on these findings, it was deemed that the APES 40-61 sequence (22 nucleotides) conserved regardless of species would contribute as a microRNA to higher antibody production.

Example 6

Example of Higher Growth Resulting from Strong Expression of APES in a Host Cell for Antibody Production From a host cell for antibody production DXB11/TAUT, a highly antibody-producing cell (DXB11/TAUT/MAM) that produced 3.9 g/L of MAb1 (anti-IL-6R antibody) on the 14th day of a 1L-jar fed-batch culture was obtained. The TAUT's ability to maintain survival rate helped the production of 8.1 g/L on the 31st day of the culture, but it was necessary to increase the highest cell density (4.1×10e6 cells/mL) to achieve high production on the 14th day of the culture, considering actual production. If the suppressed Nfkbia mRNA expression resulting from the strong expression of APES (Example 4) promotes the activation of Nfkb, the expression of growth-related gene would be increased, and thus, the highest cell density would be possibly increased. A plasmid for co-expression of APES and a plasmid for co-expression of ALT1 which contributed to higher antibody production as is the case with APES (pPur-APES165, pPur-ALT1, respectively; FIG. 17) were each introduced into the above highly antibody-producing cell DXB11/TAUT/MAb1 (parent strain). The top three most highly grown strains each for the two types were selected and subjected to a shaker fed-batch culture. As a result, the average value of the highest cell density was (11.5±1.7)× 10e6 cells/mL for the strongly APES165-expressing cell, showing that more highly grown cell than the strongly ALT1-expressing cell ((8.9±1.8)×10e6 cells/mL) was obtained. Further, the average values of the amounts of antibody production on the 14th day of the shaker fed-batch culture were 4.4±0.6 g/L for the strongly APES-expressing cell and 4.0±0.6 g/L for strongly ALT1-expressing cell, which were higher than 3.4 g/L for the DXB11/TAUT/MAb1 cell into which a plasmid had not yet been introduced. This result shows that the strongly APES-expressing effect was positively produced independently of the strongly TAUT-expressing effect (FIG. 18). The positive effect resulting from the strong expression of APES was markedly observed in a 1L-jar fed-batch culture. The comparison of highly grown cells in the shaker fed-batch culture revealed the highest growth of the strongly APES-expressing strain, which showed its advantage of high producibility in a short-term culture, with the value of 5.3 g/L on the 12th day of the culture as compared with 3.2 g/L for the parent strain and 4.4 g/L for the strongly ALT1-expressing strain (FIG. 19). Based on the above results, the present inventors decided to modify the host cell for antibody production DXB11/TAUT into a host cell that exhibits higher growth, and prepared a strongly APES165-expressing host cell DXB11/TAUT/APES. Gene introduction was performed by introducing pPur-APES165 into the DXB11/TAUT host by means of electroporation. For the nine candidate host strains that were good in both survival rate and growth after drug selection, their expression levels of APES snRNA (small non-coding RNA) in subculture were quantified. The DXB11/TAUT/APES candidate host strain that expressed APES at a high level had a high viable cell density during the culture and showed a correlation ($R^2=0.70$) (FIG. 20).

Example 7

Example 2 of Higher Production Resulting from Strong Expression of APES in Antibody-Producing Cells As is the case with Example 3, plasmids expressing 5' end partial sequences of the AI462015 transcript were introduced into strongly MAb1-expressing DXB11s cells, and their antibody-producing potentials were compared.

In addition to APES4-168 (APES165), expression units of APES4-68 (SEQ ID NO: 5) and APES69-133 (SEQ ID NO: 6), each of which consisted of a partial sequence of APES4-168, were prepared to study the antibody-producing potentials of the cells. Compared with strong null vector expression (null), APES4-68 and APES69-133 exhibited high antibody production with significant differences of $p<0.05$ and $p<0.01$, respectively (t-test, $P<0.001$, FIG. 21).

FIG. 22 shows which regions the respective partial sequences having APES activity that were identified in Examples 3 and 7 correspond to in the mouse AI462015 transcript. The partial sequences exhibiting APES activity comprise at least 23 nucleotides of the Nfkbia complementary sequence.

Example 8

Gene Analysis Related to APES

Based on the gene information at the time of filing this application, it is stated in Example 1 that "AI462015 is an mRNA type non-coding RNA of 437 nucleotides and its sequence exists on the complementary strand near the 3' untranslated region (56590831-56590397) of the NfkBia gene in mouse genome 12". However, the subsequent information update given by GeneBank revealed that the 437 nucleotides, which are the AI462015 transcript, correspond to the complementary strand of the 3' untranslated region (513 nucleotides) of the mouse NfkBia gene (FIG. 23). As shown in FIG. 24, there is AI462015 homologous sequence on the genome sequence of CHO-K1 cells that was published after the tiling of this application (SEQ ID NO: 25: AI462015; SEQ ID NOs: 26-27: CHO-K1 genome). Further, the suppression of the Nfkbia expression was observed in highly antibody-producing CHO cells (Example 4). Hence, it is conceivable that AI462015 homologous sequence is expressed at a high level in CHO cells and functions therein.

The present invention can be applied to any cells producing a recombinant polypeptide such as an antibody.

All publications, patents and patent applications cited herein are incorporated herein by reference in their entirety.

The invention claimed is:

1. A method of producing an antibody comprising culturing a cell into which a DNA encoding a desired antibody and APES (Antibody Production Enhancing Sequence) have been exogenously introduced by transfection, thereby producing the desired antibody, wherein
the APES is a nucleic acid molecule that increases the ability of the cultured cells to produce the antibody, wherein the APES is selected from nucleic acid molecules each consisting of any of the following nucleotide sequences:
(a) a DNA consisting of the nucleotide sequence of any of SEQ ID NOs:1 to 16 and 29;
(b) a DNA consisting of 19 to 25 nucleotides in the sequence of SEQ ID NO: 2;
(c) an RNA that is a transcript of (a), or (b); and
(d) a DNA or RNA consisting of a sequence that can bind 19 to 25 nucleotides in the sequence of SEQ ID NO: 2 by base pairing.

2. The method according to claim 1, wherein the APES has been introduced into the cell by an expression vector.

3. The method according to claim 1, wherein the cell into which the APES has been artificially introduced is a cell in which the transcription of endogenous APES has been activated.

4. The method according to claim 1, wherein the method further comprises introducing a DNA encoding a taurine transporter.

5. The method according to claim 1, wherein the method further comprises introducing a DNA encoding cysteine sulfinic acid.

6. The method according to claim 1, wherein the method further comprises introducing a DNA encoding alanine transferase.

7. The method according to claim 1, wherein the cell is a Chinese hamster ovary cell.

8. A method of producing a pharmaceutical composition comprising an antibody, wherein the method comprises producing an antibody by the method according to claim 1, and mixing the antibody with a pharmaceutically acceptable carrier or additive.

* * * * *

SEQUENCE LISTING

```
<160> NUMBER OF SEQ ID NOS: 48

<210> SEQ ID NO 1
<211> LENGTH: 437
<212> TYPE: DNA
<213> ORGANISM: Mus musculus

<400> SEQUENCE: 1
tttgtctgta aaaatctgtt taataaatat acatcttaga agtaccaaaa taattaccaa        60
caaaatacaa catatacaac atttacaaga aggcgacaca gaccttagtt gggggcgact       120
```

```
tttaagcaca tgccactgaa cacctggctc ttacatggga ggacacactg ggctcactta    180
ctaggtctat ggtggttcaa tcaaaagcac aataaataaa acgtggtcct ttcattaggt    240
tctggaaaat cacctccccc cccccaaaa aaaatcccac aaacatgaac cttaagagac    300
attttctttg aatttcagtg atctgttttcc ccgatttca caaagacaac agccgaatca    360
ccccagtaaa atgcctgggt ctaggcgctg tgtggtgtgg tgctaagtat accctttctc    420
attttttttc ttttttct                                                    437

<210> SEQ ID NO 2
<211> LENGTH: 165
<212> TYPE: DNA
<213> ORGANISM: Artificial Sequence
<220> FEATURE:
<223> OTHER INFORMATION: Description of Artificial Sequence: Synthetic
      APES165 polynucleotide

<400> SEQUENCE: 2
gtctgtaaaa atctgtttaa taaatataca tcttagaagt accaaaataa ttaccaacaa     60
aatacaacat atacaacatt tacaagaagg cgacacagac cttagttggg ggcgactttt    120
aagcacatgc cactgaacac ctggctctta catgggagga cacac                    165

<210> SEQ ID NO 3
<211> LENGTH: 434
<212> TYPE: DNA
<213> ORGANISM: Artificial Sequence
<220> FEATURE:
<223> OTHER INFORMATION: Description of Artificial Sequence: Synthetic
      APES434 polynucleotide

<400> SEQUENCE: 3
gtctgtaaaa atctgtttaa taaatataca tcttagaagt accaaaataa ttaccaacaa     60
aatacaacat atacaacatt tacaagaagg cgacacagac cttagttggg ggcgactttt    120
aagcacatgc cactgaacac ctggctctta catgggagga cacactgggc tcacttacta    180
ggtctatggt ggttcaatca aaagcacaat aaataaaacg tggtcctttc attaggttct    240
ggaaaatcac ctcccccccc cccaaaaaaa atcccacaaa catgaacctt aagagacatt    300
ttctttgaat ttcagtgatc tgttttcccccg gatttcacaa agacaacagc cgaatcaccc    360
cagtaaaatg cctgggtcta ggcgctgtgt ggtgtggtgc taagtatacc ctttctcatt    420
tttttctttt ttct                                                       434

<210> SEQ ID NO 4
<211> LENGTH: 130
<212> TYPE: DNA
<213> ORGANISM: Artificial Sequence
<220> FEATURE:
<223> OTHER INFORMATION: Description of Artificial Sequence: Synthetic
      APES130 polynucleotide

<400> SEQUENCE: 4
gtctgtaaaa atctgtttaa taaatataca tcttagaagt accaaaataa ttaccaacaa     60
aatacaacat atacaacatt tacaagaagg cgacacagac cttagttggg ggcgactttt    120
aagcacatgc                                                            130

<210> SEQ ID NO 5
<211> LENGTH: 65
<212> TYPE: DNA
<213> ORGANISM: Artificial Sequence
```

```
<220> FEATURE:
<223> OTHER INFORMATION: Description of Artificial Sequence: Synthetic
      APES 4-68 oligonucleotide

<400> SEQUENCE: 5
gtctgtaaaa atctgtttaa taaatataca tcttagaagt accaaaataa ttaccaacaa    60
aatac                                                                65

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      APES 69-133 oligonucleotide

<400> SEQUENCE: 6
aacatataca acatttacaa gaaggcgaca cagaccttag ttggggcga cttttaagca     60 catgc                                                                65

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      APES 40-91 oligonucleotide

<400> SEQUENCE: 7
aagtaccaaa ataattacca acaaaataca acatatacaa catttacaag aa            52

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      APES 40-68 oligonucleotide

<400> SEQUENCE: 8
aagtaccaaa ataattacca acaaaatac                                      29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      APES 40-63 oligonucleotide

<400> SEQUENCE: 9
aagtaccaaa ataattacca acaa                                           24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      APES 40-61 oligonucleotide

<400> SEQUENCE: 10
aagtaccaaa ataattacca ac                                             22

<210> SEQ ID NO 11
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      APES 69-91 oligonucleotide

<400> SEQUENCE: 11
aacatataca acatttacaa gaa                                               23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 84-104 oligonucleotide

<400> SEQUENCE: 12
tacaagaagg cgacacagac c                                                 21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      APES 99-119 oligonucleotide

<400> SEQUENCE: 13
acagacctta gttgggggcg ac                                                22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 101-121 oligonucleotide

<400> SEQUENCE: 14
gaccttagtt gggggcgact t                                                 21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      APES 71-91 oligonucleotide

<400> SEQUENCE: 15
catatacaac atttacaaga a                                                 21

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      APES 71-112 oligonucleotide

<400> SEQUENCE: 16
catatacaac atttacaaga aggcgacaca gaccttagtt gg                          42

<210> SEQ ID NO 17
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
acttggtgac tttgggtgct                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcctccaaac acacagtcat                                              20

<210> SEQ ID NO 19
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide-part of Hamster Nfkbia mRNA

<400> SEQUENCE: 19
agtacccgga tacagcagca gctgggccag ctgacccggg aaaatcttca gatgctgccc    60
gagagtgagg atgaggagag ctacgacaca gagtcagaat tcacggagga tgagctgccc   120
tatgatgact gtgtgtttgg aggca                                        145

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cagctgaccc gggaaaatc                                               19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgactctgtg tcgtagctct cctc                                         24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tcagatgctg cccgagagtg agga                                         24
```

<210> SEQ ID NO 23
<211> LENGTH: 1394
<212> TYPE: DNA
<213> ORGANISM: Mus musculus

<400> SEQUENCE: 23

| | | | | | | |
|---|---|---|---|---|---|---|
| ctctgggctc | gaatggcatg | ggggacagct | tttatatggt | taactccgcc | cgttttatga | 60 |
| ctagaaccaa | tagttttta | tgccaaatgc | actgaaatcc | cctaatttgc | aaagccaaac | 120 |
| gcccctatg | tgagtaatac | ggggactttt | tacccaattt | cccaagcgga | aagccccta | 180 |
| atacactcat | atggcatatg | aatcagcacg | gtcatgcact | ctaatggcgg | cccatagga | 240 |
| ctttccacat | aggggcgtt | caccatttcc | cagcatagg | gtggtgactc | aatggcctt | 300 |
| acccaagtac | attgggtcaa | tgggaggtaa | gccaatgggt | ttttcccatt | actggcaagc | 360 |
| acactgagtc | aaatgggact | ttccactggg | tttgcccaa | gtacattggg | tcaatgggag | 420 |
| gtgagccaat | gggaaaaacc | cattgctgcc | aagtacactg | actcaatagg | actttccaa | 480 |
| tgggttttc | cattgttggc | aagcatataa | ggtcaatgtg | ggtgagtcaa | tagggacttt | 540 |
| ccattgtatt | ctgccagta | cataaggtca | atagggggtg | aatcaacagg | aaagtcccat | 600 |
| tggagccaag | tacactgcgt | caataggac | tttccattgg | gttttgccca | gtacataagg | 660 |
| tcaataggg | atgagtcaat | gggaaaaacc | cattggagcc | aagtacactg | actcaatagg | 720 |
| gactttccat | tgggttttgc | ccagtacata | gggtcaatag | gggtgagtc | aacaggaaag | 780 |
| ttccattgga | gccaagtaca | ttgagtcaat | agggactttc | caatgggttt | tgcccagtac | 840 |
| ataaggtcaa | tgggaggtaa | gccaatgggt | ttttcccatt | actggcacgt | atactgagtc | 900 |
| attagggact | ttccaatggg | ttttgcccag | tacataaggt | caataggggt | gaatcaacag | 960 |
| gaaagtccca | ttggagccaa | gtacactgag | tcaatagga | ctttccattg | ggttttgccc | 1020 |
| agtacaaaag | gtcaatgggg | ggtgagtcaa | tgggttttc | ccattattgg | cacgtacata | 1080 |
| aggtcaatag | gggtgagtca | ttgggttttt | ccagccaatt | taattaaaac | gccatgtact | 1140 |
| ttcccaccat | tgacgtcaat | gggctattga | aactaatgca | acgtgacctt | taaacggtac | 1200 |
| tttcccatag | ctgattaatg | ggaaagtacc | gttctcgagc | caatacacgt | caatgggaag | 1260 |
| tgaagggca | gccaaaacgt | aacaccgccc | cggttttccc | ctggaaattc | catattggca | 1320 |
| cgcattctat | tggctgagct | gcgttctacg | tgggtataag | aggcgcgacc | agcgtcggta | 1380 |
| ccgtcgcagt | cttg | | | | | 1394 |

<210> SEQ ID NO 24
<211> LENGTH: 24
<212> TYPE: DNA
<213> ORGANISM: Homo sapiens

<400> SEQUENCE: 24

| | |
|---|---|
| ttgttggtaa ttattttggt actt | 24 |

<210> SEQ ID NO 25
<211> LENGTH: 433
<212> TYPE: DNA
<213> ORGANISM: Mus musculus

<400> SEQUENCE: 25

| | | | | | | |
|---|---|---|---|---|---|---|
| tgtctgtaaa | aatctgttta | ataaatatac | atcttagaag | taccaaaata | attaccaaca | 60 |
| aaatacaaca | tatacaacat | ttacaagaag | gcgacacaga | ccttagttgg | gggcgacttt | 120 |
| taagcacatg | ccactgaaca | cctggctctt | acatgggagg | acacactggg | ctcacttact | 180 |

```
aggtctatgg tggttcaatc aaaagcacaa taaataaaac gtggtccttt cattaggttc      240
tggaaaatca cctcccccc ccccaaaaaa atcccacaa acatgaacct taagagacat       300
tttctttgaa tttcagtgat ctgtttcccc ggatttcaca aagacaacag ccgaatcacc      360
ccagtaaaat gcctgggtct aggcgctgtg tggtgtggtg ctaagtatac cctttctcat      420
tttttttctt ttt                                                         433

<210> SEQ ID NO 26
<211> LENGTH: 414
<212> TYPE: DNA
<213> ORGANISM: Cricetulus griseus

<400> SEQUENCE: 26
tgtctgtaaa atctgttta ataaatatac atcttagaag taccaaaata attaccaaca       60
aaatacacca tatacaacat ttacaagagg gtaacaaaaa cctcagtcgg gagtgactag     120
cacataccac tcaacacctg gttctacatg tgaggacata ccaggctcag ctaccagatc     180
taccgttcag tcaaaagcac aataaataga atgtggtccc tttcatcagt ctggaaaacc     240
acctcccaaa acctcacgaa tgtgagcttt aaaagacatt ttctttgaat tccaatgatc     300
tgtttcccca tttcacaaaa ataacaatct gccatcacca gagtaagatg cttgggggca    360
ggctgtgtgc agtgtggtgg taagtatatc cctttctttc ttttttttct tctt          414

<210> SEQ ID NO 27
<211> LENGTH: 414
<212> TYPE: DNA
<213> ORGANISM: Cricetulus griseus

<400> SEQUENCE: 27
aagaagaaaa aaagaaaga aagggatata cttaccacca cactgcacac agcctgcccc       60
caagcatctt actctggtga tggcagattg ttatttttgt gaaatgggga aacagatcat     120
tggaattcaa agaaaatgtc ttttaaagct cacattcgtg aggttttggg aggtggtttt    180
ccagactgat gaaagggacc acattctatt tattgtgctt ttgactgaac ggtagatctg    240
gtagctgagc ctggtatgtc ctcacatgta gaaccaggtg ttgagtggta tgtgctagtc    300
actcccgact gaggttttg ttaccctctt gtaaatgttg tatatggtgt attttgttgg     360
taattatttt ggtacttcta agatgtatat ttattaaaca gatttttaca gaca           414

<210> SEQ ID NO 28
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide-part of Hamster Nfkbis mRNA (134bp)

<400> SEQUENCE: 28
agtacccgga tacagcagca gctgggccag ctgacccggg aaaatcttca gatgctgccc       60
gagagtgagg atgaggagag ctacgacaca gagtcagaat tcacggagga tgagctgccc      120
tatgatgact gtgt                                                        134

<210> SEQ ID NO 29
<211> LENGTH: 85
<212> TYPE: DNA
<213> ORGANISM: Artificial Sequence
<220> FEATURE:
<223> OTHER INFORMATION: Description of Artificial Sequence: Synthetic
``` conserved oligonucleotide 7-91

<400> SEQUENCE: 29
tgtaaaaatc tgtttaataa atatacatct tagaagtacc aaaataatta ccaacaaaat    60
acaacatata caacatttac aagaa                                          85

<210> SEQ ID NO 30
<211> LENGTH: 83
<212> TYPE: DNA
<213> ORGANISM: Homo sapiens

<400> SEQUENCE: 30
tgtaaaaatc tgtttaataa atatacatca taaaagtacc aaaataatta ccaacaatac    60
attatgtaca ccatttacag gag                                            83

<210> SEQ ID NO 31
<211> LENGTH: 85
<212> TYPE: DNA
<213> ORGANISM: Rattus norvegicus

<400> SEQUENCE: 31
tgtaaaaatc tgtttaataa atatacatct tagaagtacc aaaataatta ccaacaaaat    60
acaccatata caacatttac aagaa                                          85

<210> SEQ ID NO 32
<211> LENGTH: 89
<212> TYPE: DNA
<213> ORGANISM: Pan troglodytes

<400> SEQUENCE: 32
tgtaaaaatc tgtttaataa atatacatca taaaagtacc aaaataatta ctaacaatac    60
attatgtaca tcatttacag gagggtaac                                      89

<210> SEQ ID NO 33
<211> LENGTH: 89
<212> TYPE: DNA
<213> ORGANISM: Macaca mulatta

<400> SEQUENCE: 33
tggaaaaatc tgtttaataa atatacataa taaaagtacc aaaataatta ccaacaatac    60
actatgtaca ccatttacag aagggtaac                                      89

<210> SEQ ID NO 34
<211> LENGTH: 90
<212> TYPE: DNA
<213> ORGANISM: Bos taurus

<400> SEQUENCE: 34
tgtaaaaatc tgtttaataa atatacatct taaaagtacc aaaataatta ctgacaaaat    60
acactatgta cactatttac aggaggggaa                                     90

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      kB motif oligonucleotide

<400> SEQUENCE: 35

-continued gggactttcc                                                           10

<210> SEQ ID NO 36
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
agtacccgga tacagcagca gctgggccag ctgacccggg aaaatcttca gatgctgccc     60
gagagtgagg atgaggagag ctacgacaca gagtcagaat tcacggagga tgagctgccc    120
tatgatgact gtgt                                                     134

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaattccgcc                                                           10

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
attatccagc tg                                                        12

<210> SEQ ID NO 39
<211> LENGTH: 437
<212> TYPE: DNA
<213> ORGANISM: Mus musculus

<400> SEQUENCE: 39
tttgtctgta aaatctgttt aataaatat acatcttaga agtaccaaaa taattaccaa      60
caaaatacaa catatacaac atttacaaga aggcgacaca gaccttagtt gggggcgact    120
tttaagcaca tgccactgaa cacctggctc ttacatggga ggacacactg ggctcactta    180
ctaggtctat ggtggttcaa tcaaaagcac aataaataaa acgtggtcct ttcattaggt    240
tctggaaaat cacctccccc cccccaaaa aaaatcccac aaacatgaac cttaagagac    300
attttctttg aatttcagtg atctgtttcc ccggatttca caaagacaac agccgaatca    360
ccccagtaaa atgcctgggt ctaggcgctg tgtggtgtgg tgctaagtat acccttctc    420 atttttttc tttttct                                                   437

<210> SEQ ID NO 40
<211> LENGTH: 433
<212> TYPE: DNA
<213> ORGANISM: Mus musculus

<400> SEQUENCE: 40
tgtctgtaaa aatctgttta ataaatatac atcttagaag taccaaaata attaccaaca    60

```
aaatacaaca tatacaacat ttacaagaag gcgacacaga ccttagttgg gggcgacttt      120
taagcacatg ccactgaaca cctggctctt acatgggagg acacactggg ctcacttact      180
aggtctatgg tggttcaatc aaaagcacaa taaataaaac gtggtccttt cattaggttc      240
tggaaaatca cctccccccc ccccaaaaaa aatcccacaa acatgaacct taagagacat      300
tttctttgaa tttcagtgat ctgtttcccc ggatttcaca aagacaacag ccgaatcacc      360
ccagtaaaat gcctgggtct aggcgctgtg tggtgtggtg ctaagtatac cctttctcat      420 ttttttttctt ttt                                                        433
```

<210> SEQ ID NO 41
<211> LENGTH: 83
<212> TYPE: DNA
<213> ORGANISM: Homo sapiens

<400> SEQUENCE: 41

```
tgtaaaaatc tgtttaataa atatacatca taaaagtacc aaaataatta ccaacaatac       60
attatgtaca ccatttacag gag                                               83
```

<210> SEQ ID NO 42
<211> LENGTH: 85
<212> TYPE: DNA
<213> ORGANISM: Rattus norvegicus

<400> SEQUENCE: 42

```
tgtaaaaatc tgtttaataa atatacatct tagaagtacc aaaataatta ccaacaaaat       60
acaccatata caacatttac aagaa                                             85
```

<210> SEQ ID NO 43
<211> LENGTH: 89
<212> TYPE: DNA
<213> ORGANISM: Pan troglodytes

<400> SEQUENCE: 43

```
tgtaaaaatc tgtttaataa atatacatca taaaagtacc aaaataatta ctaacaatac       60
attatgtaca tcatttacag gagggtaac                                         89
```

<210> SEQ ID NO 44
<211> LENGTH: 89
<212> TYPE: DNA
<213> ORGANISM: Macaca mulatta

<400> SEQUENCE: 44

```
tggaaaaatc tgtttaataa atatacataa taaaagtacc aaaataatta ccaacaatac       60
actatgtaca ccatttacag aagggtaac                                         89
```

<210> SEQ ID NO 45
<211> LENGTH: 90
<212> TYPE: DNA
<213> ORGANISM: Bos taurus

<400> SEQUENCE: 45

```
tgtaaaaatc tgtttaataa atatacatct taaaagtacc aaaataatta ctgacaaaat       60
acactatgta cactatttac aggaggggaa                                        90
```

<210> SEQ ID NO 46
<211> LENGTH: 13
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 46
aaaaaaaaaa aaa                                                              13

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 47
tttttttttt tttvn                                                            15

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttttttttt ttt                                                              13
```